United States Patent
Hasegawa et al.

(10) Patent No.: US 6,258,232 B1
(45) Date of Patent: Jul. 10, 2001

(54) GAS COMPONENT CONCENTRATION MEASURING APPARATUS

(75) Inventors: Jun Hasegawa; Yukihiro Yamashita, both of Kariya; Tomomichi Mizoguchi, Nagoya; Masayuki Takami, Kariya, all of (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 09/218,083

(22) Filed: Dec. 22, 1998

(30) Foreign Application Priority Data

Dec. 25, 1997 (JP) .................................................... 9-358524
Dec. 25, 1997 (JP) .................................................... 9-358525

(51) Int. Cl.[7] ................................................. G01N 27/407
(52) U.S. Cl. ......................... 204/424; 73/23.32; 219/497
(58) Field of Search ................................. 204/424, 425, 204/426, 427, 428, 429, 408; 123/697; 73/23.32; 219/490, 497

(56) References Cited

U.S. PATENT DOCUMENTS

| | | | |
|---|---|---|---|
| 4,524,264 | * 6/1985 | Takeuchi et al. | 219/497 |
| 4,708,777 | * 11/1987 | Kuraoka | 204/424 |
| 4,721,088 | * 1/1988 | Mieno et al. | 123/697 |
| 5,419,828 | 5/1995 | Nakano et al. . | |
| 5,656,190 | * 8/1997 | Aoki | 219/505 |
| 5,700,367 | 12/1997 | Yamada et al. . | |
| 5,709,198 | 1/1998 | Sagisaka et al. . | |
| 5,782,227 | * 7/1998 | Abe | 123/689 |
| 5,852,228 | * 12/1998 | Yamashita et al. | 73/23.32 |
| 6,009,866 | * 1/2000 | Sagisaka et al. | 123/681 |

FOREIGN PATENT DOCUMENTS 61-274249  12/1986  (JP) .
7-325066   12/1995  (JP) .

* cited by examiner

Primary Examiner—Robert J. Warden, Sr.
Assistant Examiner—Kaj K. Olsen
(74) Attorney, Agent, or Firm—Nixon & Vanderhye PC

(57) ABSTRACT

A sensor element of an A/F sensor is constructed to laminate and integrate a solid electrolyte and a heater. The A/F sensor outputs a linear A/F detection signal proportional to the oxygen concentration in exhaust gases, when voltage is applied. An ECU controls the heater through heater control circuit to keep the sensor element at a predetermined activation temperature. The ECU detects an element resistance on the basis of the voltage applied to the sensor element and sensor current caused by the applied voltage, and converts the element resistance to an element temperature. During the temperature increasing of the A/F sensor, the current supply to the heater is duty-controlled according to the element temperature changing rate (the temperature increasing rate of the sensor element). Accordingly, the temperature increasing characteristics of the sensor is satisfactorily maintained, and disadvantages such as an element cracking are prevented.

24 Claims, 27 Drawing Sheets

GAS COMPONENT CONCENTRATION MEASURING APPARATUS

CROSS REFERENCE TO RELATED APPLICATIONS

This application is based upon and claims priority from Japanese patent application Nos. Hei 9-358524 filed Dec. 25, 1997 and Hei 9-358525 filed Dec. 25, 1997, the entire contents of which are incorporated herein by reference.

BACKGROUND OF THE INVENTION

1. Field of the Invention

The present invention relates to a gas component concentration measuring apparatus, and more particularly, to a gas component concentration measuring apparatus for detecting an oxygen concentration in gases to be measured, such as exhaust gases from an engine.

2. Description of Related Art

In an automotive engine, for example, the air/fuel ratio control is generally executed based on a detection result of an oxygen concentration (or an air/fuel ratio) by an oxygen concentration sensor. This oxygen concentration sensor has a solid electrolyte made of zirconia, and the temperature of the sensor element (or the solid electrolyte) has to be kept at a predetermined activation temperature so as to detect the oxygen concentration (or the air/fuel ratio) accurately with the solid electrolyte. Usually, a heater is attached to the sensor thereby to control its activation. A method for this heater control, as known per se, is to control the electric power fed to the heater or to feedback-control the temperature of the sensor element to a predetermined activation temperature.

In the related art described above, however, at a cold start of the engine, for example, the sensor element (or the solid electrolyte) is increased as soon as possible from the cold state. However, if the temperature of the sensor element is rapidly increased, certain disadvantages, such as an element or heater cracking or a separation of the bonded faces of the element and the heater, may result.

Furthermore, in recent years, there is a tendency that a regulation on the exhaust gas component of the engine is intensified more and more from the standpoint of environmental protection, and it has been desired to improve the detection accuracy and durability of the oxygen concentration sensor. According to the aforementioned related art, however, the individual differences or aging of the sensor compromise the sensor accuracy. This problem is caused by an excess or shortage of the heater calorific power necessary for maintaining the sensor activation state. In other words, if the heater has a poor calorific power, the desired sensor activation state cannot be maintained, and the sensor detection accuracy is compromised. On the other hand, an excessive calorific power deteriorates the sensor element or the heater.

SUMMARY OF THE INVENTION

The present invention was made in light of the foregoing problems, and it is an object of the present invention to provide a gas component concentration measuring apparatus that maintains the sensor characteristics for the temperature increase and reduces the aforementioned-problems such as element cracking.

It is another object of the present invention to provide a gas component concentration measuring apparatus which improves the detection accuracy and durability by controlling the heater in a system which keeps the sensor active state with the heat of the heater.

The gas component concentration measuring apparatus of the present invention includes: a sensor for measuring the concentration of a specific component of gases, including a sensor element made of a solid electrolyte; a heater for heating the sensor element to a predetermined activation temperature, when activated by a power supply voltage; and a heater control circuit for controlling the current supply amount to the heater in accordance with the temperature increasing rate of the sensor element.

Accordingly, an excessive temperature increase in the sensor element can be suppressed by controlling the heater current while monitoring the temperature increasing rate of the sensor element. By monitoring the temperature increasing rate, moreover, a quick activation of the sensor is achieved. As a result, the sensor characteristics for temperature increase is satisfactorily maintained, and disadvantages such as element cracking is prevented.

The invention has a prominent effect especially in a laminated type sensor in which the heater is laminated on the sensor element having the solid electrolyte thereby to integrate the solid electrolyte and the heater. More specifically, the laminated type sensor may have problems such as element cracking or heater cracking because the solid electrolyte and the heater are located close to each other. According to the present invention, however, such problems are prevented.

The "temperature increasing rate of the sensor element" means a velocity of the temperature increase of the solid electrolyte or the heater. In order to control the temperature increasing rate of the sensor element, the heater current may be controlled according to the changing rate of the element temperature or the element resistance.

In order to control the temperature increasing rate of the sensor element, the heater current may be controlled according to the difference between the element temperature and the heater temperature.

In order to control the temperature increasing rate of the sensor element, the heater current may be controlled according to the changing rate of the heater temperature or the heater resistance.

According to another aspect of the present invention, it includes: a sensor including a sensor element made of a solid electrolyte for measuring the concentration of a specific component of gases; and a heater for generating heat when a current is supplied by a power supply. The sensor element is heated to a predetermined activation temperature by supplying the current to the heater. Supplying current to the heater is compensated according to a duration from the cold state to the activation of the sensor.

Accordingly, it is possible to control the current supply to the heater while considering the individual difference and aging of the sensor. Therefore, the control accuracy is improved. In short, when the sensor is deteriorated, the element temperatures (or the temperature of the solid electrolyte) before and after the deterioration differ even for an identical heater current control. According to the present invention, on the contrary, an unexpected fluctuation of the element temperature is reduced. As a result, the heater is controlled to improve the detection accuracy and the durability of the sensor.

BRIEF DESCRIPTION OF THE DRAWINGS

Other features and advantages of the present invention will be appreciated, as well as methods of operation and the function of the related parts, from a study of the following detailed description, the appended claims, and the drawings, all of which form a part of this application. In the drawings:

DESCRIPTION OF THE PREFERRED EMBODIMENTS (First Embodiment)

A first embodiment of the present invention will be described with reference to the accompanying drawings. An air/fuel ratio detecting device in this embodiment is applied to an electronic control gasoline injection engine to be mounted on an automobile. In an air/fuel ratio control system of the engine, a fuel injection amount of the engine is controlled to a desired air/fuel ratio on the basis of the detected result by the air/fuel ratio detecting device. Here will be described in detail on an air/fuel ratio (A/F) detection routine using an air/fuel ratio sensor (A/F sensor) and a heater current control routine for a heater attached to the A/F sensor.

Figure 1:
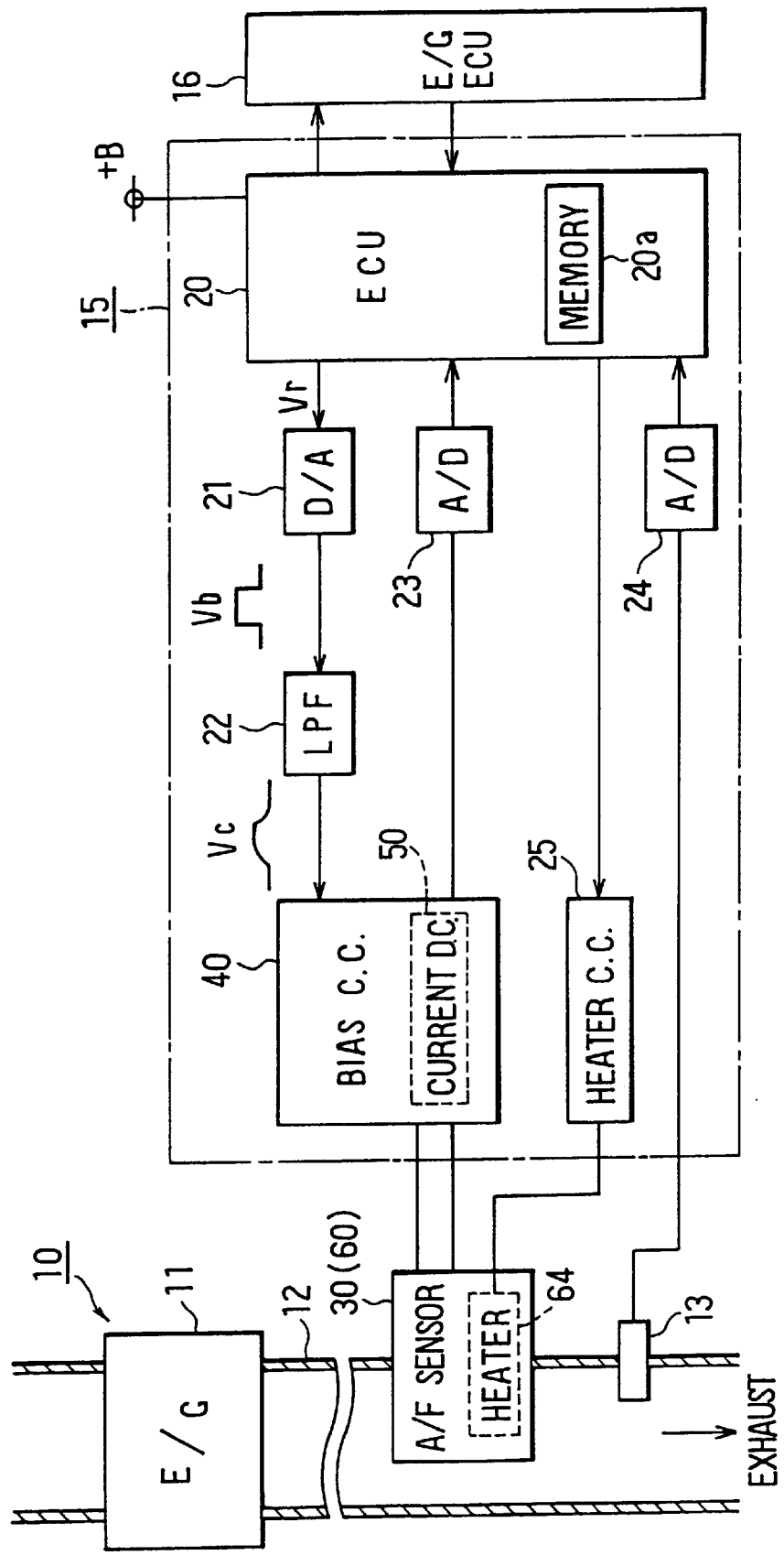
FIG. 1 is a schematic diagram showing the entire construction of an air/fuel ratio control system according to first to third embodiments of the present invention.

In FIG. 1, an air/fuel ratio detecting device 15 is equipped with a microcomputer (as will be shortly referred to as the "ECU") 20 as its pivotal component for internal operations. This ECU 20 is connected for bidirectional communications with an engine control ECU 16 for realizing controls for the fuel injection or ignition. A limiting current type air/fuel ratio sensor (hereinafter referred to as the "A/F sensor") 30 is mounted on an exhaust pipe 12 leading from the engine body 11 of an engine 10, so that it may output a linear A/F detection signal (or a sensor current signal) proportional to the oxygen concentration in the exhaust gases in accordance with the application of a voltage, as commanded by the ECU 20.

The ECU 20 is constructed to include a CPU, a ROM and a RAM, as well known in the art, for executing various operations, and controls a bias control circuit 40 and a heater control circuit 25, as will be specified, in accordance with a predetermined control program. The ECU 20 is started with the power of a battery power source +B and is equipped therein with a backup memory 20*a* for latching the stored content even when the electric power supply is broken (i.e., IG=OFF).

Figure 3:
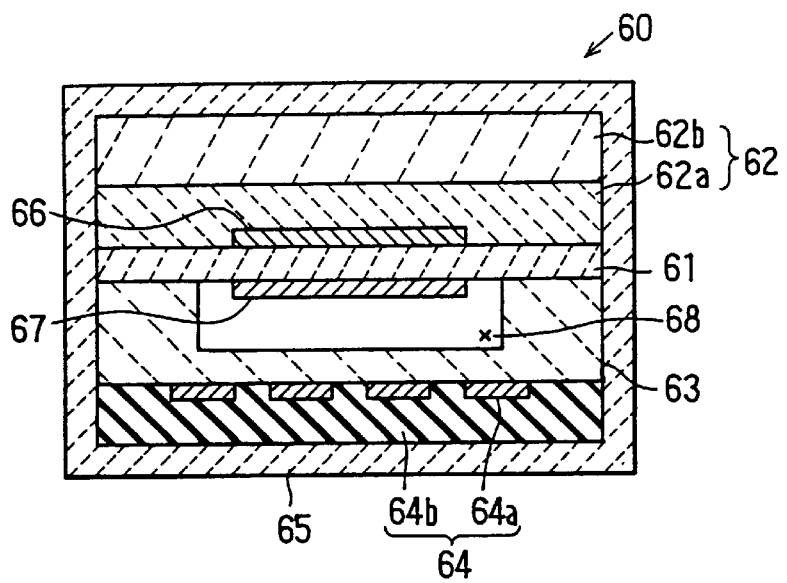
FIG. 3 is a sectional view showing a sensor element in the first to third embodiments of the present invention.
Figure 4:
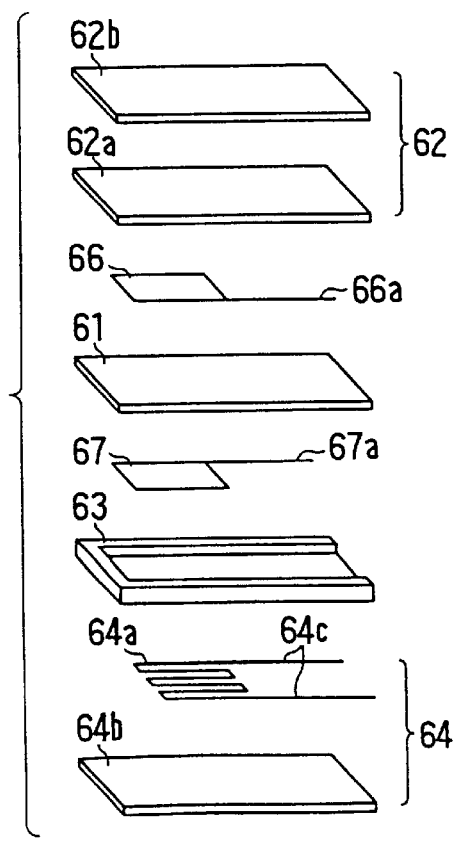
FIG. 4 is an exploded perspective view showing the individual members of the sensor element in the first to third embodiments of the present invention.

The A/F sensor 30 is equipped with a laminated type sensor element (or cell) 60, as will be described with reference to FIGS. 2 to 4.

Figure 2:
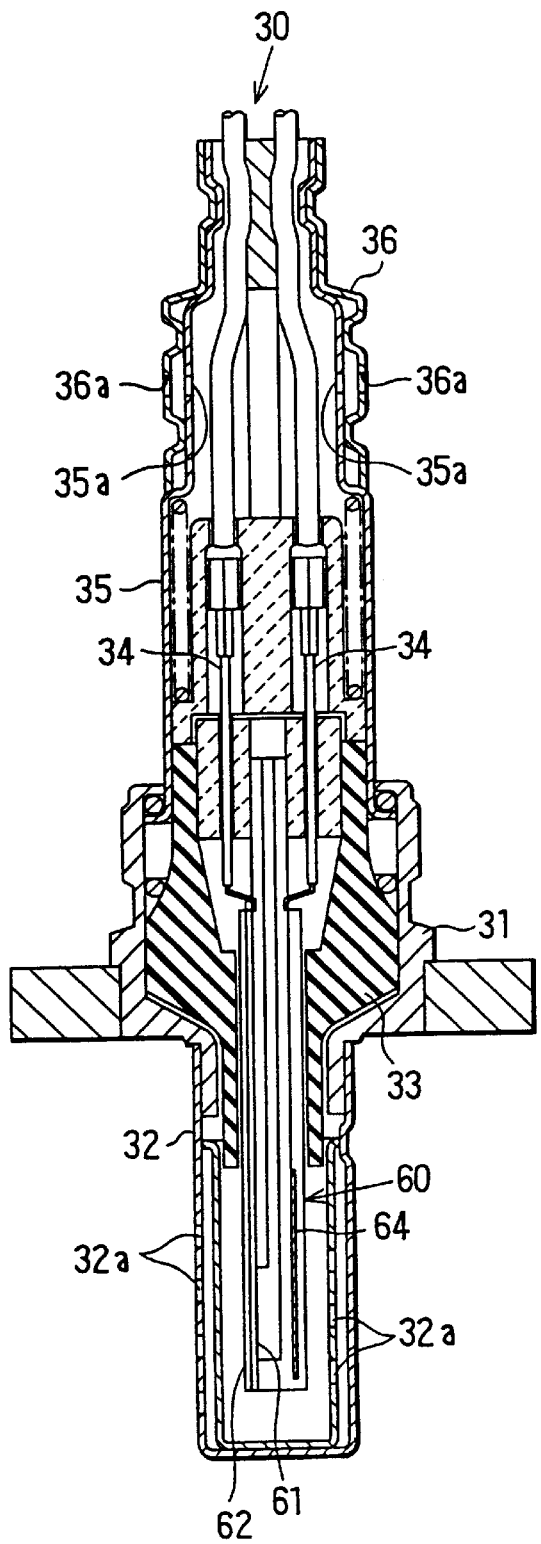
FIG. 2 is a sectional view showing the entire construction of an A/F sensor in the first to third embodiments of the present invention.

As shown in FIG. 2, the A/F sensor 30 has cylindrical metal housing 31 to be screwed in the exhaust pipe wall, and an element cover 32 is mounted on the lower side opening of the housing 31. In the element cover 32, a leading end (or a lower end) of the sensor element 60 having a shape of a long plate is located. The element cover 32 is made into a bottomed double structure having a plurality of exhaust ports 32*a* for introducing the exhaust gases into the element cover 32.

The sensor element 60 is extended upward through an insulating member 33 arranged in the housing 31, and its upper end portion is connected with a pair of lead wires 34.

To the upper end of the housing 31, there is caulked a body cover 35, over which a dust cover 36, so that the upper sensor portion is protected by the double structure of those body cover 35 and dust cover 36. In these covers 35 and 36, respectively, there are formed pluralities of air ports 35*a* and 36*a* for introducing the atmosphere into the covers.

Next, the construction of the sensor element 60 will be described with reference to FIGS. 3 and 4. The sensor element 60 is constructed to include a solid electrolyte 61, a gas diffusion resistive layer 62, an atmosphere introduction duct 63 and a heater 64, as coarsely divided, by laminating them. These components are enclosed by a protective layer 65.

The strip-shaped solid electrolyte 61 is made of a sheet of partially stabilized zirconia and is screen-printed on its upper face (as located on the side of the gas diffusion resistive layer 62) with a porous metering electrode 66 of platinum or the like and on its lower face (as located on the side of the atmosphere introduction duct 63) with a porous atmospheric. electrode 67 of platinum or the like. The metering electrode 66 and the atmospheric electrode 67 are connected with lead wires 66*a* and 67*a*.

The gas diffusion resistive layer 62 is formed of a gas permeable layer 62*a* made of a porous sheet for introducing the exhaust gases into the metering electrode 66 and a gas shielding layer 62*b* made of a dense layer for suppressing the permeation of the exhaust gases. Both the gas permeable layer 62*a* and the gas shielding layer 62*b* are sheet-molded of ceramics of alumina, spinel or zirconia and are given different permeabilities in accordance with the average diameter and the porosity.

The atmosphere introduction duct 63 is made of highly thermally conductive ceramics such as alumina to form an atmospheric chamber 68. The atmosphere introduction duct 63 plays a role to introduce the atmosphere into the atmospheric electrode 67 in the atmospheric chamber 68. Here, this atmospheric chamber 68 has communication with the air ports 35*a* and 36*a* of the covers 35 and 36, as shown in FIG. 2.

On the lower face of the atmosphere introduction duct 63, there is mounted the heater 64. This heater 64 is composed of a heating element 64*a* for generating a heat when activated by the battery power supply +B, and an insulating sheet 64*b* covering the heating element 64*a*. Lead wires 64*c* are connected with the two ends of the heating element 64*a*. However, the invention should not be limited to the construction of FIG. 3, but its construction could be modified such that the heating element 64*a* is buried in the solid electrolyte 61 or such that the heating element 64*a* is buried in the gas diffusion resistive layer 62.

In the sensor element 60, the exhaust gases that reach the metering electrode 66 penetrate not perpendicularly to the gas permeable layer 62*a* (or longitudinally of the Drawings) but in parallel with the gas permeable layer 62*a*. In other words, the surface of this gas permeable layer 62*a* is covered with the gas shielding layer 62*b* so that the exhaust gases can penetrate into the permeable layer 62*a* not in the vertical direction but in the horizontal direction. In this case, the amount of gas diffusion in the gas permeable layer 62*a* depends on the transverse size (i.e., the distance between the side face of the gas permeable layer 62*a* and the metering electrode 66). Since this size can be easily and freely set, however, a homogeneous and stable sensor output can be obtained even with a dispersed porosity of the gas permeable layer 62*a*.

In the A/F sensor 30 thus constructed, the sensor element 60 generates a limiting current according to the oxygen concentration in a region leaner than the stoichiometric air/fuel ratio. In this case, the sensor element 60 (or the solid electrolyte 61) can detect the oxygen concentration with the linear characteristics. Since a temperature as high as about 600° C. or more is required for activating the sensor element 60 and since this sensor element 60 has a narrow range for the activation temperature, the active state cannot be maintained by the heating action of the exhaust gases of the engine 10 only. In this embodiment, therefore, the sensor element 60 is held within the activation temperature range by the heating control of the heater 64 (or the heating element 64*a*). Here in a regionricherthan the stoichiometric air/fuel ratio, the concentration of the unburned gases such as carbon monoxide (CO) changes substantially linearly with the air/fuel ratio so that the sensor element 60 generates a limiting current according to the concentration of the Co or the like.

Figure 5:
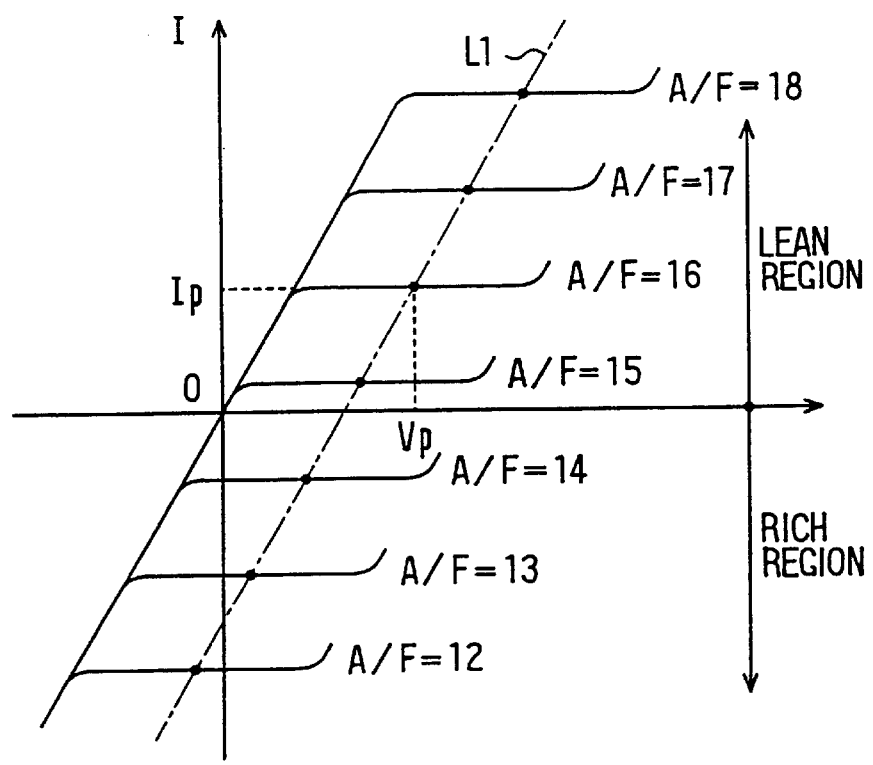
FIG. 5 is a voltage-current characteristics diagram of the A/F sensor in the first to third embodiments of the present invention.

The voltage-current characteristics of the A/F sensor 30 will be described with reference to FIG. 5. As shown in FIG. 5, there is a linear relationship between the electric current Ip which flows into the solid electrolyte 61 of the sensor element 60 and the applied voltage applied to the solid electrolyte 61. In FIG. 5, the flat portions parallel to the voltage axis (the abscissa) specify the limiting current of the sensor element 60, and the increase/decrease in this limiting current (the sensor current) corresponds to the increase/decrease of the A/F (that is the extent of lean/rich). In short, the limiting current increases as the A/F becomes leaner, and it decreases as the A/F becomes richer.

In the voltage-current characteristics, the regions of voltages, which are lower than the straight portions parallel to the voltage axis, present resistance dominant regions, in which the gradient of linear portions is specified by the internal resistance (as called the "element resistance") of the solid electrolyte 61 in the sensor element 60. This element resistance changes with the temperature such that the above-specified gradient decreases with the increase in the element resistance as the temperature of the sensor element 60 lowers.

Figure 6:
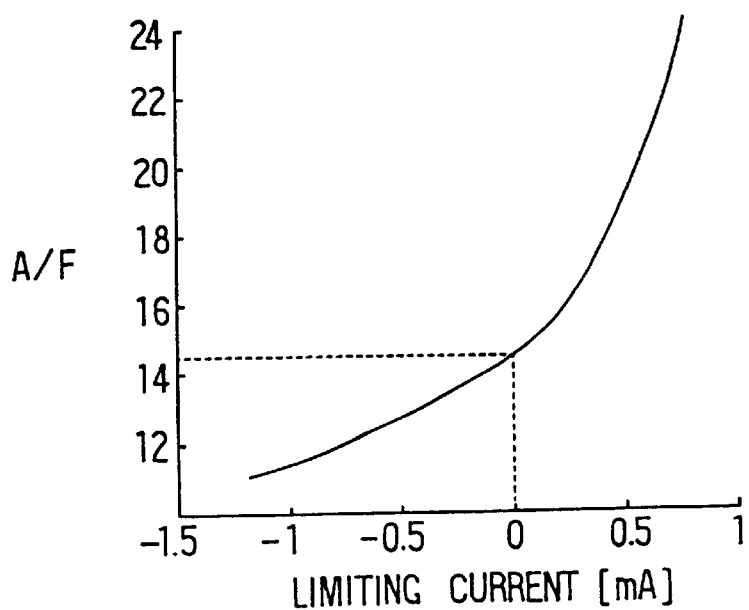
FIG. 6 is a graph illustrating a relation between the limiting current and the air/fuel ratio of the A/F sensor in the first to third embodiments of the present invention.

FIG. 6 is a graph plotting a relationship between the limiting current value on the abscissa and the A/F, corresponding to the limiting current value, on the ordinate.

Moreover, the heat resisting characteristics of the A/F sensor 30 are exemplified by the following specific numerical values:

Heat Resistance Temperature of the Element =900 to 950° C.;

Heat Resistance Temperature of the Heater =1,000 to 1,100° C.;

Maximum Value of Element Temperature Changing Rate =150 to 200° C./s;

Maximum Value of Heater Temperature Changing Rate =200° C./s; and

Maximum Value of Temperature Difference Between Element and Heater =200° C.

In FIG. 1, on the other hand, a bias command signal (or a digital signal) Vr for applying the voltage to the A/F sensor 30 (or its sensor element 60) is inputted to a D/A converter 21 from the ECU 20 and is converted thereby into an analog signal Vb, and this analog signal Vb is inputted to an LPF (Low Pass Filter) 22. Moreover, an output voltage Vc, which is prepared by filtering out the high-frequency component of the analog signal Vb through the LPF 22, is inputted to the bias control circuit 40 for applying a voltage for detecting the A/F or the element resistance to the A/F sensor 30. At the time of detecting the A/F, a chain line L1 of FIG. 5 is employed to set an applied voltage Vp corresponding to the prevailing A/F. At the time of detecting the element resistance, on the other hand, there is applied a voltage which is composed of the so-called "frequency signal" and has a predetermined single time constant.

A current detecting circuit 50 in the bias control circuit 40 detects the value of a current which flows when the voltage is applied to the A/F sensor 30. The analog signal having the current value, as detected in the current detecting circuit 50, is inputted through an A/D converter 23 to the ECU 20. The heater 64 (or its heating element 64a), as mounted in the A/F sensor 30, is operationally controlled by the heater control circuit 25. In short, this heater control circuit 25 performs the duty control of the amount of electricity to the heater 64 in accordance with the element or heater temperature of the A/F sensor 30 thereby to control the heating of the heater 64.

On the engine exhaust pipe 12, moreover, there is mounted an exhaust temperature sensor 13 for detecting the exhaust gas temperature. The output of this sensor 13 is inputted through an A/D converter 24 to the ECU 20.

Figure 7:
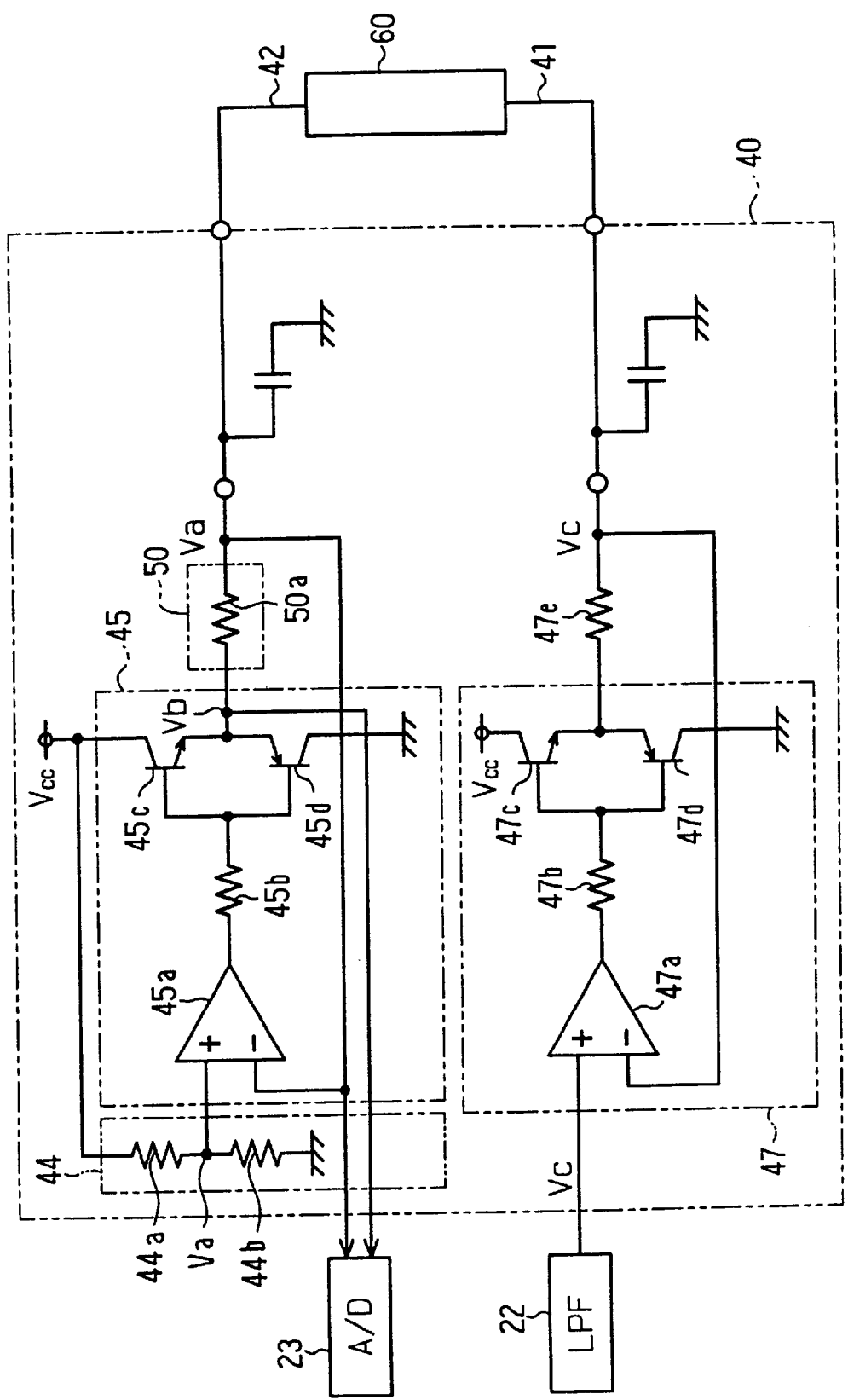
FIG. 7 is an electric circuit diagram showing a detailed construction of a bias control circuit in the first embodiment of the present invention.

Next, the construction of the bias control circuit 40 will be described with reference to an electric circuit diagram of FIG. 7. In FIG. 7, the bias control circuit 40 is constructed to include a reference voltage circuit 44, a first voltage feeding circuit 45, a second voltage feeding circuit 47 and the current detecting circuit 50, as coarsely divided. The reference voltage circuit 44 divides a constant voltage Vcc with voltage dividing resistors 44a and 44b to generate a constant reference voltage Va.

The first voltage feeding circuit 45 is constructed of a voltage follower circuit and feeds the same voltage Va as the reference voltage Va of the reference voltage circuit 44 to one terminal (as connected to the atmospheric electrode 67 of FIG. 3) of the sensor element 60. More specifically, the first voltage feeding circuit 45 is composed of: an operational amplifier 45a connected at its positive input terminal with the voltage dividing point between the voltage dividing resistors 44a and 44b and connected at its negative input terminal with the one terminal 42 of the sensor element 60; a resistor 45b connected at its one terminal with the output terminal of the operational amplifier 45a; and an NPN transistor 45c and a PNP transistor 45d connected at their individual bases with the other terminal of the resistor 45b. The NPN transistor 45c is connected at its collector with the constant voltage Vcc and at its emitter with the one terminal 42 of the sensor element 60 through the current detecting resistor 50a of the current detecting circuit 50. On the other hand, the PNP transistor 45d is connected at its emitter with the emitter of the NPN transistor 45c and is earthed at its collector.

The second voltage feeding circuit 47 is also constructed of a voltage follower circuit to feed the same voltage Vc as the output voltage Vc of the LPF 22 to the other terminal 41 (as connected with the metering electrode 66 of FIG. 3) of the sensor element 60. More specifically, the second voltage feeding circuit 47 is composed of: an operational amplifier 47a connected at its positive input terminal with the output of the LPF 22 and at its negative input terminal with the other terminal 41 of the sensor element 60; a resistor 47b connected at its one terminal with the output terminal of the operational amplifier 47a; and an NPN transistor 47c and a PNP transistor 47d connected at their individual bases with the other terminal of the resistor 47b. The NPN transistor 47c is connected at its collector with the constant voltage Vcc and at its emitter with the other terminal 41 of the sensor element 60 through a resistor 47e. On the other hand, the PNP transistor 47d is connected at its emitter with the emitter of the NPN transistor 47c and is earthed at its connector.

With the construction thus far described, the one terminal 42 of the sensor element 60 is fed at all times with the constant voltage Va. When the voltage Vc lower than the constant voltage Va is fed to the other terminal 41 of the sensor element 60 through the LPF 22, moreover, the sensor element 60 is positively biased. When the voltage Vc higher than the constant voltage Va is fed to the other terminal 41 of the sensor element 60 through the LPF 22, on the other hand, the sensor element 60 is negatively biased.

Figure 8:
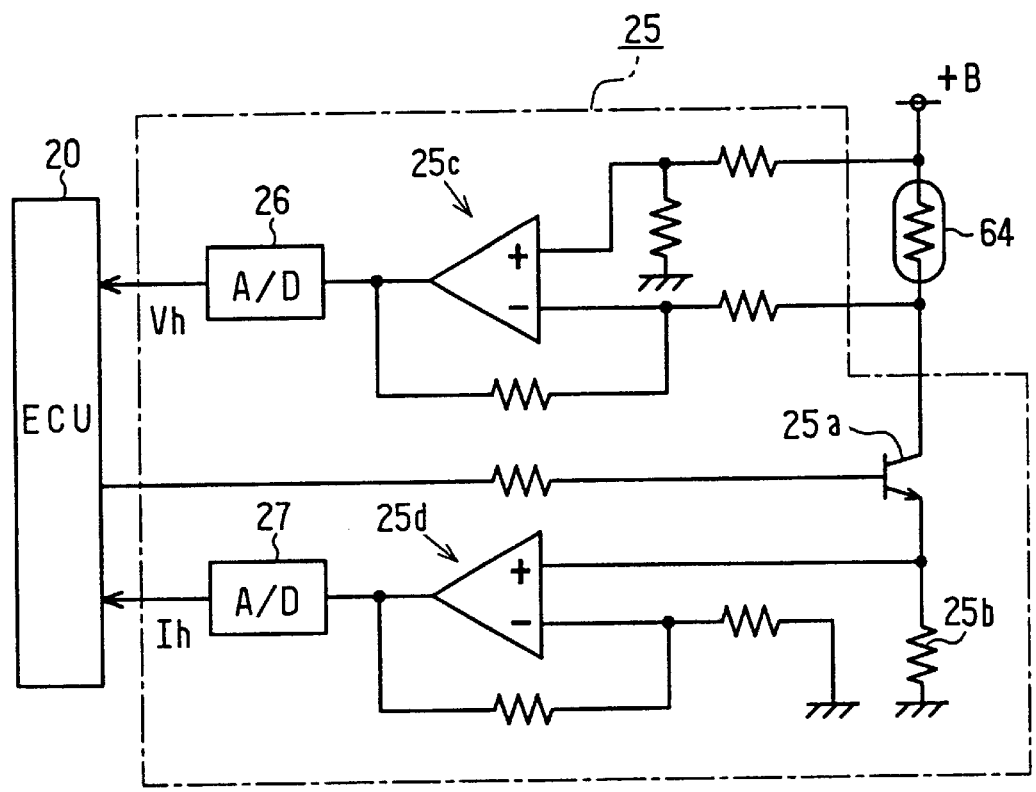
FIG. 8 is an electric circuit diagram showing a detailed construction of a heater control circuit according to the first embodiment of the present invention.

FIG. 8 is a circuit diagram showing a construction of the heater control circuit 25.

In FIG. 8, the heater 64 (or its heating element 64a) is connected at its one terminal with the battery power supply +B and at its other terminal with the collector of a transistor 25a composing a switching element. This transistor 25a is earthed at its emitter through a heater current detecting resistor 25b. The heater voltage Vh is detected in terms of the potential difference between the two terminals of the heater 64, and the detected result is inputted to the ECU 20 through an operational amplifier 25c and the A/D converter 26. On the other hand, the heater current Ih is detected in terms of the potential difference between the two terminals of the heater current detecting resistor 25b, and the detected result is inputted to the ECU 20 through the operational amplifier 25d and the A/D converter 27.

Operation of the air/fuel ratio detecting device 15 will now be described.

Figure 9A:
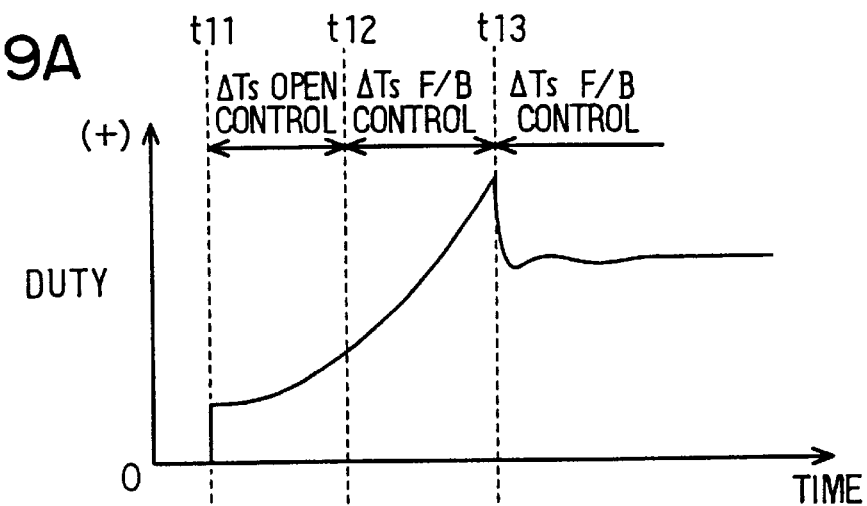
FIGS. 9A to 9C are time charts for explaining the operations of an air/fuel ratio detecting device according to the first embodiment of the present invention.
Figure 9B:
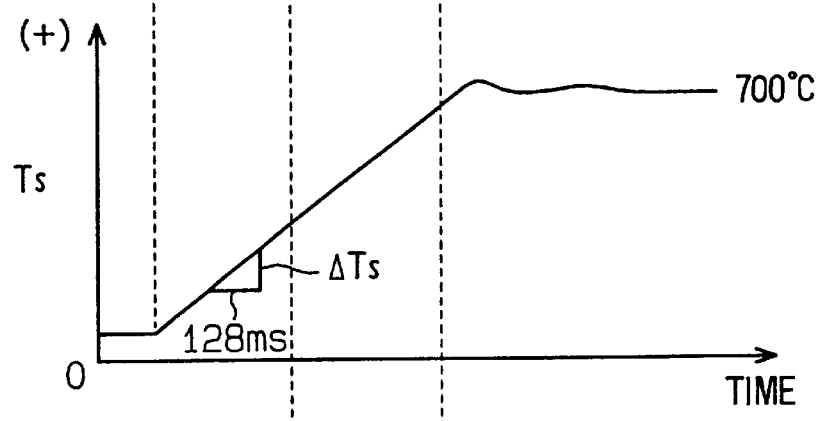
Figure 9C:
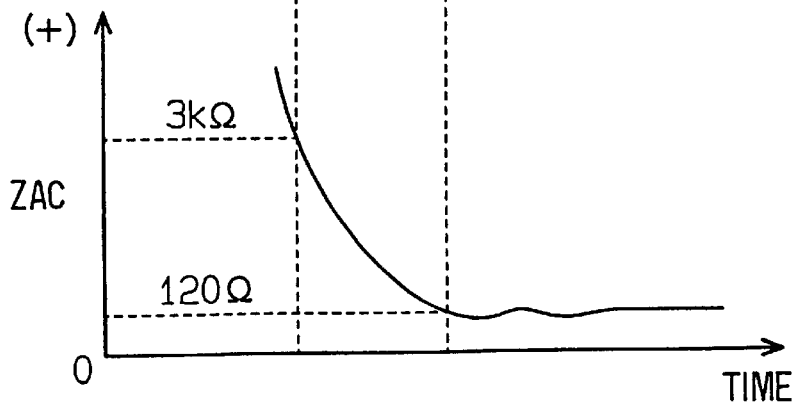

First of all, the summary of the operation of this device will be described with reference to the time charts of FIGS. 9A to 9C. In FIGS. 9A to 9C, there are illustrated the procedures in which the A/F sensor 30 is heated from a cold state at a cold start of the engine 10. The element resistance ZAC at the beginning of the current supply to the heater (right after the engine started) cannot be detected because it is very high at that time.

When the ignition key is turned on at time t11, an open-loop control of an element temperature changing rate ΔTs is initiated. This element temperature changing rate ΔTs is given as a temperature change amount of an element temperature Ts at unit time (e.g., every 128 ms in this embodiment). At this time, the duty of the current supply is determined by using a predetermined map such that the element temperature changing rate ΔTs is substantially constant. In short, the current supply duty for the heater 64 rises gradually with the lapse of time, and the element temperature Ts (the temperature of the solid electrolyte) rises accordingly.

At time t12 when the element resistance ZAC is lower than a predetermined level (e.g., 3 KΩ in this embodiment) in the course of the temperature rise, the heater control is switched from the prevailing open-loop control of the element temperature changing rate ΔTs to the feedback control of the element temperature changing rate ΔTs. At a time period between t12 and t13, more specifically, the current supply amount to the heater (the current supply duty) is determined by executing the feedback control of the element temperature changing rate ΔTs to the target level.

At later time t13 when the element resistance ZAC reaches down to the determined value (e.g., 120 Ω in this embodiment) of the activation completion, a series of controls for the element temperature changing rate ΔTs are terminated. In place of these controls, the feedback control, which maintains the element temperature constant, is initiated. At and after time t13, more specifically, the current supply amount to the heater (the current supply duty) is determined by executing the feedback control of the element temperature changing rate ΔTs to a predetermined target level (700° C.). Since the feedback control with the "constant element temperature" and the feedback control with the "constant element resistance" are substantially identical, the feedback control with the constant element resistance (to feedback the element resistance ZAC to the target level) is executed in this embodiment.

Figure 10:
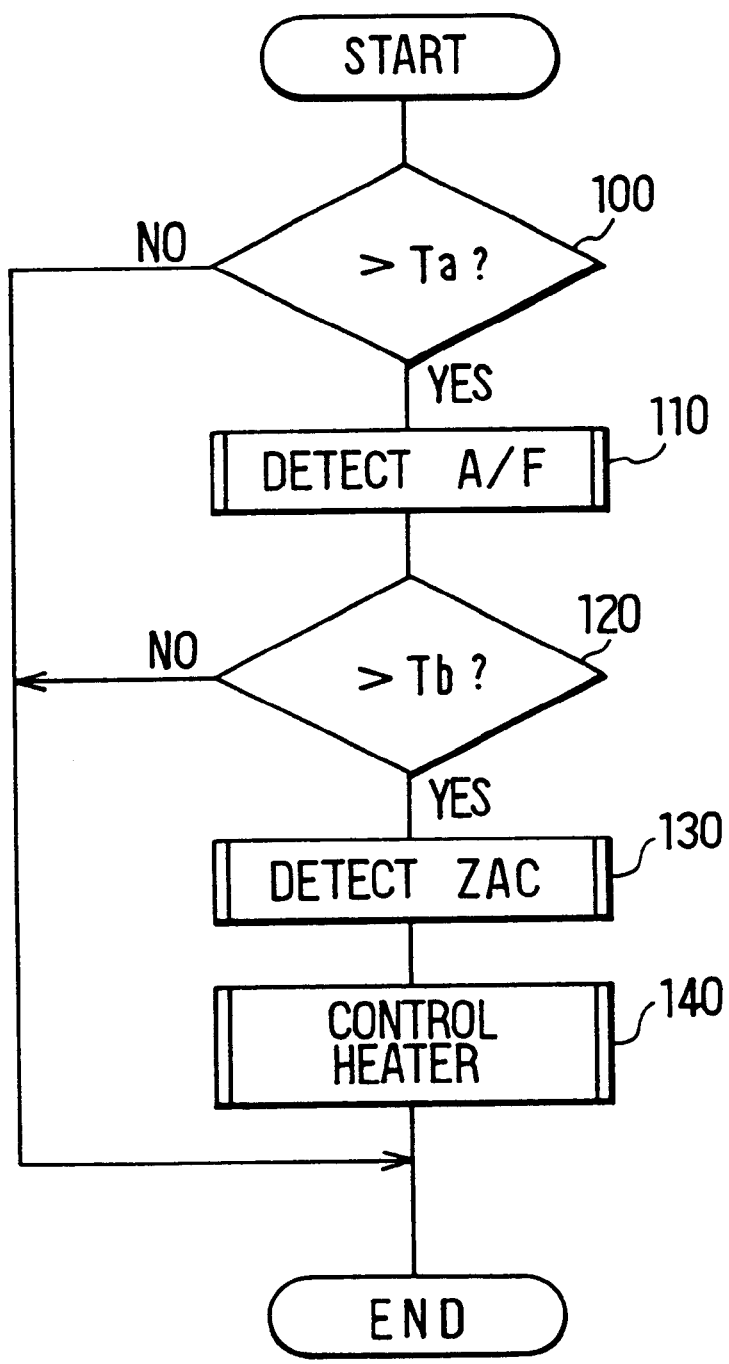
FIG. 10 is a flowchart showing a main routine of a microcomputer in the air/fuel ratio detecting device according to the first embodiment of the present invention.

FIG. 10 is a flowchart showing the summary of a main routine in the ECU 20. This routine is initiated when the ECU 20 is turned on.

As shown in FIG. 10, the ECU 20 determines in Step 100 whether a predetermined time period Ta has elapsed from the previous A/F detection. The time period Ta corresponds to an A/F detection cycle, and is set to Ta=about 4 ms, for example. When the predetermined time period Ta elapses from the previous A/F detection (that is, YES in Step 100), the ECU 20 advances to Step 110 to detect the A/F according to an A/F detection routine shown in FIG. 11. When it is determined NO in Step 100, the ECU 20 ends this routine as it is for the time being.

Figure 11:
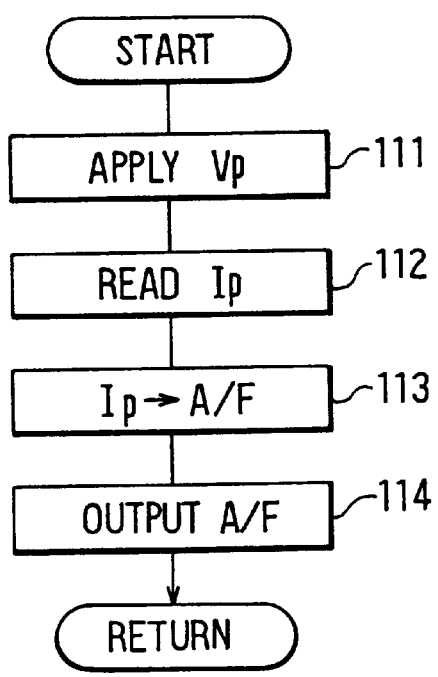
FIG. 11 is a flowchart showing an A/F detection routine according to the first embodiment of the present invention.

The A/F detection routine shown in FIG. 11 will now be described. The ECU 20 applies in Step 111 the voltage Vp to the sensor element 60 of the A/F sensor 30. The voltage Vp to be applied is set as a value, for example, on the chain line L1 in FIG. 5 according to the present air/fuel ratio (limiting current Ip).

In Step 112, the ECU 20 reads in the current, which flows through the sensor element 60 when the voltage Vp is applied, that is, the limiting current (the sensor current) Ip which is detected by the current detecting circuit 50. In Step 113, moreover, the ECU 20 converts the present limiting current Ip to corresponding A/F by using the limiting current-A/F map which is illustrated in FIG. 6. In subsequent Step 114, the ECU 20 outputs the obtained A/F to the engine control ECU 16 and then returns to the initial routine in FIG. 10.

After the A/F detection, the ECU 20 determines at Step 120 of FIG. 10 whether or not a predetermined time period Tb has elapsed from the previous detection of the element resistance. This predetermined time period Tb corresponds to the element resistance ZAC detection cycle, and is alternatively set according to the engine condition, for example. In this embodiment, the predetermined time period Tb is set variably as Tb=2 s (seconds) under an ordinary condition when the change in the A/F is relatively small (under a steady running condition of the engine 10), and as Tb=128 ms (milliseconds) when the A/F changes rapidly (at the start of the engine 10 or a transient running condition of the engine 10).

When it is determined YES in Step 120, the ECU 20 detects in Step 130 the element resistance ZAC, and executes in subsequent Step 140 the current supply control of the heater 64. The aforementioned operations of Steps 130 and 140 are executed in accordance with later-described routines shown in FIGS. 12 and 13, respectively. When it is determined NO in Step 120, the ECU 20 ends this routine as it is for the time being.

The element resistance ZAC detection routine in Step 130 of FIG. 10 will now be described with reference to FIG. 12. Here in this embodiment, for the detection of the element resistance, the "AC element resistance" is determined by using the sweep method.

Figure 12:
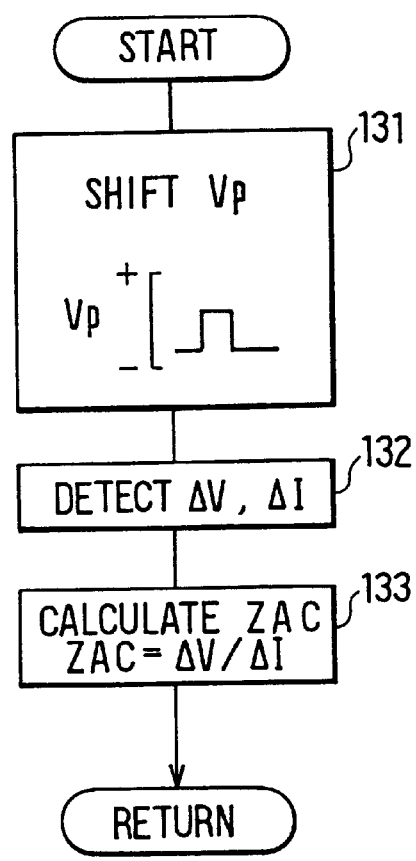
FIG. 12 is a flowchart showing a detection routine of an element resistance ZAC according to the first embodiment of the present invention.

In FIG. 12, the ECU 20 operates in Step 131 the bias command signal Vr to change the prevailing applied voltage Vp (i.e., the A/F detecting voltage) singly to the positive side. The time period for applying the voltage for detecting the element resistance is several tens to 100 μs. After this, the ECU 20 reads out in Step 132 the prevailing voltage change ΔV and a change ΔI of the sensor current detected by the current detecting circuit 50. Moreover, the ECU 20 calculates in subsequent Step 133 the element resistance ZAC from the values ΔV and ΔI (ZAC=ΔV/ΔI), and then return to the initial routine in FIG. 10.

Figure 16:
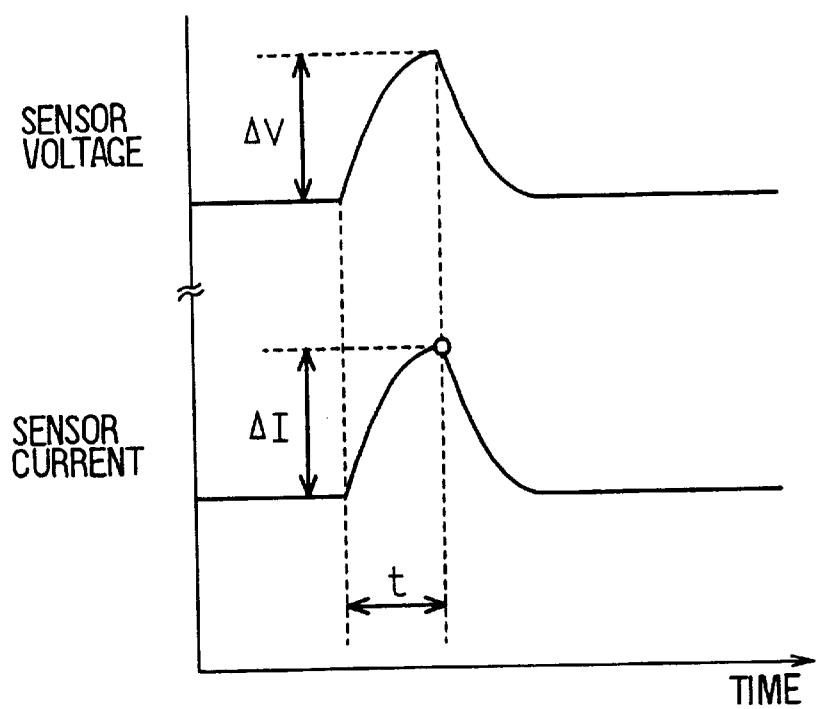
FIG. 16 is a waveform diagram illustrating a sensor voltage and a sensor current at the time of detecting the element resistance ZAC according to the first embodiment of the present invention.

According to the routine described above, the voltage, as given a predetermined time constant through the LPF 22 and the bias control circuit 40 of FIG. 1, is singly applied to the A/F sensor 30. As a result, as illustrated in FIG. 16, the peak current ΔI (i.e., the current change) is detected after lapse of time t from the application of the voltage so that the element resistance ZAC is detected from the voltage change ΔV and the peak current ΔI at this time (ZAC=ΔV/ΔI). In this case, the single voltage is applied through the LPF 22 to the A/F sensor 30 so that an excessive peak current can be suppressed to improve the accuracy for detecting the element resistance ZAC.

Figure 17:
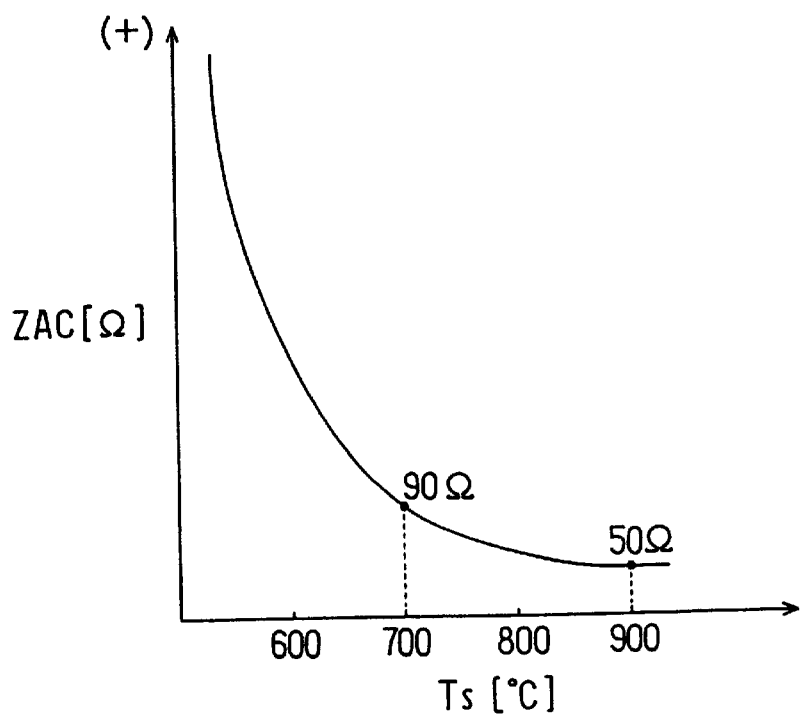
FIG. 17 is a graph illustrating a relation between the element resistance ZAC and an element temperature Ts according to the first embodiment of the present invention.

The element resistance ZAC thus determined has a relation with the element temperature Ts, as illustrated in FIG. 17. In short, the lower the element temperature Ts is, the more the element resistance ZAC drastically increases. Here, the activation temperature (e.g., about 700° C.) of the A/F sensor 30 corresponds to the element resistance ZAC of about 90Ω.

Next, a current supply control routine for the heater in Step 140 of FIG. 10 will now be described with reference to FIG. 13.

First of all, the ECU 20 determines at Step 141 whether or not the temperature of the sensor element 60 is increasing. While the temperature of the sensor element 60 is increasing (that is, when the answer of Step 141 is YES) as at a cold start of the engine 10, the ECU 20 determines at Step 142 whether or not the detected element resistance ZAC has reached a predetermined level (e.g., 3 KΩ, in this embodiment) while the temperature is increasing. Since the element resistance ZAC takes a considerable level at the beginning of the cold start of the engine 10, the ECU 20 determines that ZAC >3 KΩ, and advances to Step 143.

In Step 143, the ECU 20 executes an open-loop control of the element temperature changing rate ΔTs. Specifically, the map, as preset in the nonvolatile memory of the ECU 20, is employed to determine a duty ratio DUTY for the current supply to the heater so that the element temperature Ts may change in a predetermined profile in accordance with elapsed time period from the engine start. At the time period between t11 and t12 of FIG. 9, for example, the open-loop control of the element temperature changing rate ΔTs in Step 143 is executed.

If ZAC≦3 KΩ, on the other hand, the ECU 20 advances to Step 150, at which the element temperature changing rate ΔTs is feedback-controlled to a predetermined level in accordance with the later-described routine of FIG. 14. Specifically, the PID control method is adopted to determine the duty ratio DUTY for the current supply to the heater so that the present element temperature changing rate ΔTs conforms with the target value ΔTsref. During the time period between t12 and t13 in FIG. 9, for example, the feedback control of the element temperature changing rate ΔTs in Step 150 is executed.

After the DUTY determination in Step 143 or 150, the ECU 20 advances to Step 144, at which the duty ratio DUTY is compensated to calculate the final duty ratio Dfn. Specifically, this final duty ratio Dfn is calculated from the following formula by using a compensation value FK according to the voltage of the battery power source +B and the exhaust temperature, and the learning value FLRN according to the individual sensor difference and the aging:

Dfn=DUTY+FK+FLRN

In subsequent Step 145, moreover, the ECU 20 guards the element temperature Ts or its changing rate ΔTs within the maximum allowable value. After this, the duty ratio signal for the current supply to the heater is outputted to the heater control circuit 25 in FIG. 1.

In Step 145, it is determined whether or not the element temperature Ts exceeds the maximum allowable value "900° C." or the element temperature changing rate ΔTs exceeds the maximum allowable value "150° C./s" when the current is supplied to the heater with the calculated final duty ratio Dfn. When it is estimated that it may exceed these maximum allowable values, the current supply duty is regulated to "0" or the value (e.g., about 0.1 to 1%) for the element temperature to drop without fail. However, this duty ratio may be set according to the conversion rate of the A/D converter.

The compensation value FK is determined by summing up the compensation values FK1 to FK4, having the relations shown in FIGS. 18A to 18D:

FK=FK1+FK2+FK3+FK4.

Figure 18A:
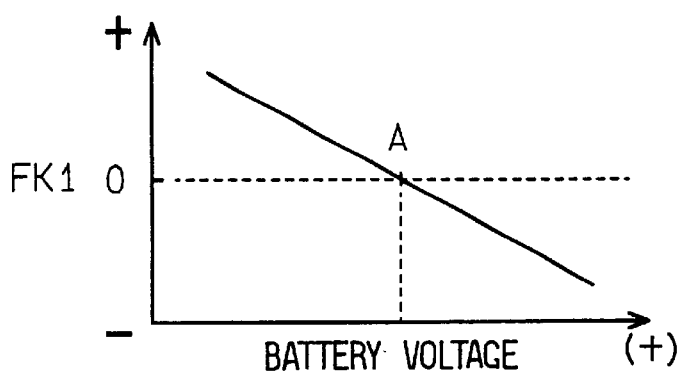
FIGS. 18A to 18D are diagrams for determining compensation values FK1 to FK4 according to the first embodiment of the present invention.

The compensation value FK1 according to the voltage level of the battery power source +B is determined from FIG. 18A. The positive compensation value FK1 is set when the battery voltage is less than or equal to A (e.g., the rated voltage of 12 V), and the negative compensation value FK1 is set when the battery voltage is greater than A.

Figure 18B:
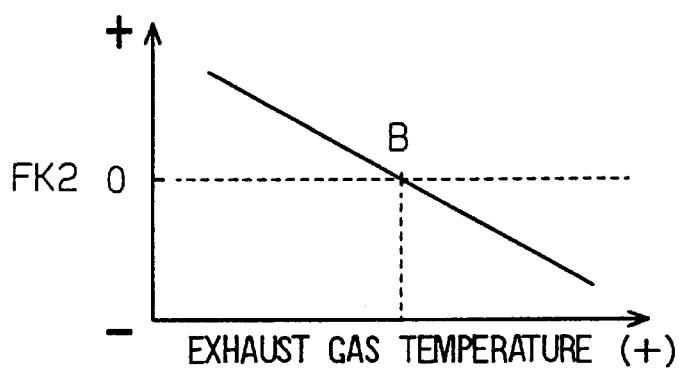

From FIG. 18B, the compensation value FK2 according to the exhaust temperature which is detected by the exhaust temperature sensor 13 is determined. The positive compensation value FK2 is set when the exhaust temperature is less than or equal to B, and the negative compensation value FK2 is set when the exhaust temperature is greater than B.

Figure 18C:
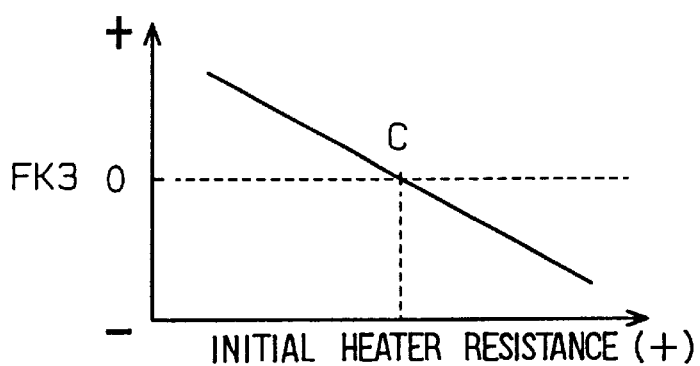

From FIG. 18C, the compensation value FK3 according to the initial heater resistance at an engine start is determined. The positive compensation value FK3 is set when the initial heater resistance is less than or equal to C, and the negative compensation value FK3 is set when the initial heater resistance is greater than C. In this case, the initial heater resistance reflects the cold state of the A/F sensor 30 at the engine start, and the compensation value FK3 may be applied only to a temperature increasing period.

Figure 18D:
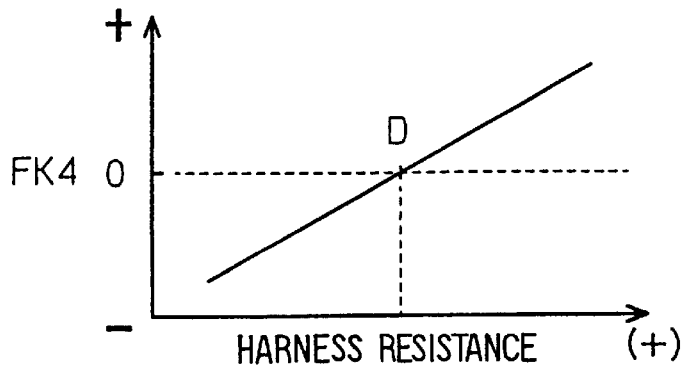

From FIG. 18D, the compensation value FK4 according to the harness resistance through the battery power supply +B, the heater 64, and the GND (see FIG. 8) is determined. The negative compensation value FK4 is set when the harness resistance is less than or equal to D, and the positive compensation value FK4 is set when the harness resistance is greater-than D.

In FIGS. 18A to 18D, a region (an insensitive band) in which the compensation value is "0" may be created in the vicinity of each of the threshold values A to D. Although the compensation value FK is set as the total of FK1 to FK4 in this embodiment, it may be set as a value containing at least one of FK1 to FK4.

The learning value FLRN is determined by summing up a first learning value FLRN1 based on a duration from the heater ON to the sensor activation, a second learning value FLRN2 based on the element resistance deviation detected at a fuel cut, and a third learning value FLRN3 based on the DUTY deviation at a steady running, as follows:

FLRN=FLRN1+FLRN2+FLRN3

These learning values FLRN1 to FLRN3 are the data which are stored in the backup memory 20a of the ECU 20 and sequentially updated. A calculation routine for these learning values FLRN1 to FLRN3 will be described hereinafter.

Figure 13:
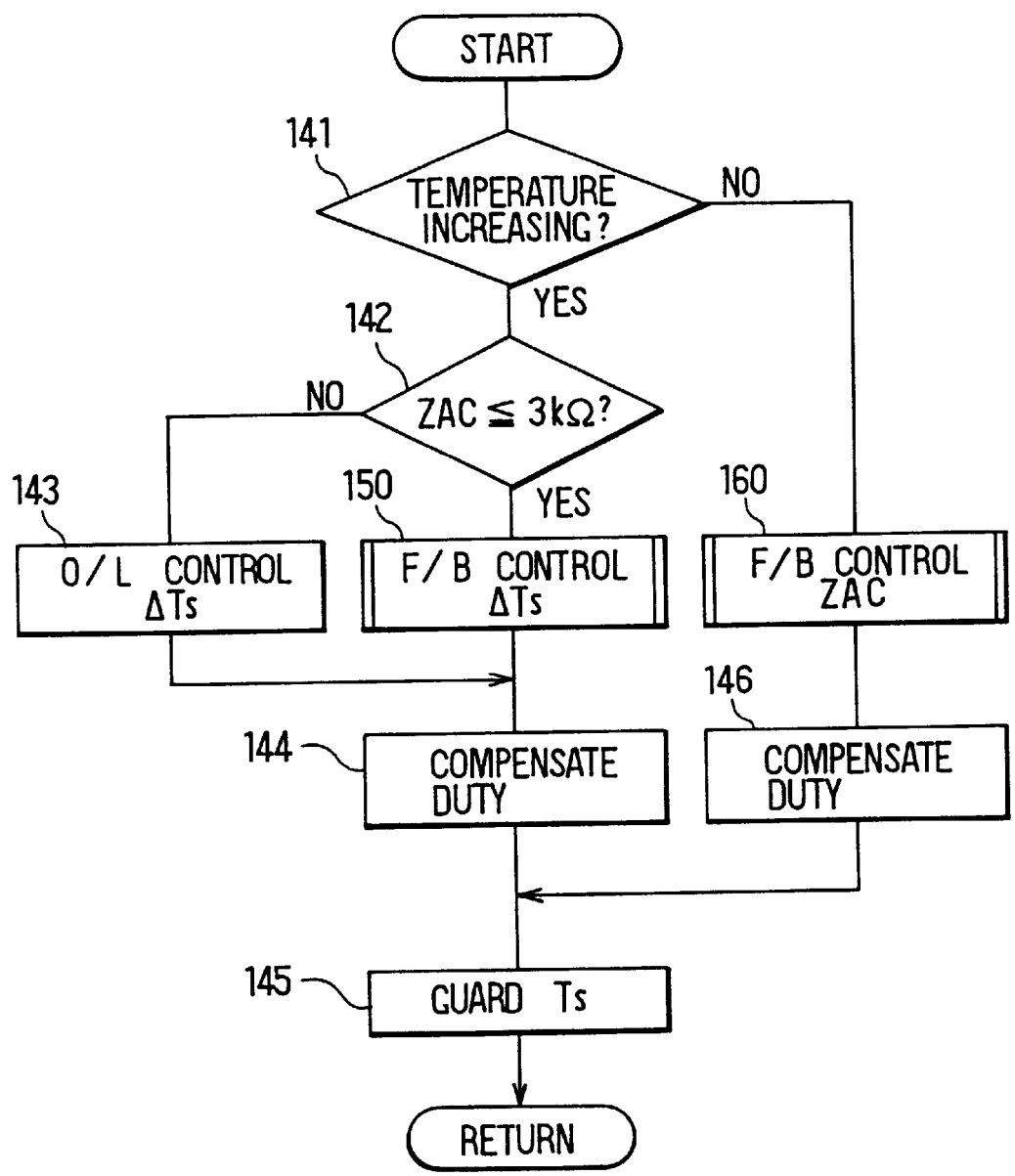
FIG. 13 is a flowchart showing a control routine of a heater current according to the first embodiment of the present invention.

When it is determined NO in Step 141 of FIG. 13 (that is, when the temperature of the sensor element 60 is not increasing), the ECU 20 advances to Step 160. In Step 160, the feedback control is executed to hold the element resistance ZAC at a predetermined value in accordance with the later-described routine shown in FIG. 15. Specifically, the duty ratio DUTY for the current supply to the heater is determined by adopting the PID control method such that the present element resistance ZAC conforms with its target value ZACref. At and after time t13 in FIG. 9, for example, the feedback control with the constant element resistance (with the constant element temperature) in Step 160 is executed.

After this, the ECU 20 advances to Step 146, at which the final duty ratio Dfn is calculated by adding the compensation value FK and the learning value FLRN to the determined duty ratio DUTY (Dfn=DUTY+FK+FLRN). In Step 145, the ECU 20 guards the element temperature TS or its changing rate ΔTs with the maximum allowable value. After this, the duty ratio signal is outputted to the heater control circuit 25 in FIG. 1.

The routine shown in FIG. 14 (i.e., the operation of Step 150 in FIG. 13) will now be described. The ECU 20 sets at Step 151 the element temperature Ts of the preceding routine to the previous value "Ts0" and the element temperature changing rate ΔTs of the preceding routine to the previous value "ΔTs0". In subsequent Step 152, moreover, the ECU 20 reads out the detected element resistance ZAC (i.e., the detected value in FIG. 12), and determines the present value of the element temperature Ts from the element resistance ZAC in accordance with the relation of FIG. 17. In Step 153, moreover, the ECU 20 calculates the present value ΔTs of the element temperature changing rate by subtracting the previous value Ts0 from the present value Ts of the element temperature (ΔTs=Ts−Ts0).

After this, the ECU 20 calculates at Step 154 a proportional term Gp, an integration term Gi and a differentiation term Gd from the following Formulas:

$$Gp = Kp \cdot (\Delta Tsref - \Delta Ts);$$
$$Gi = Gi + Ki \cdot (\Delta Tsref - \Delta Ts);$$
and
$$Gd = Kd \cdot (\Delta Ts0 - \Delta Ts).$$

In these Formulas: "Kp" represents a proportional constant; "Ki" represents an integration constant; and "Kd" a differentiation constant.

In Step 155, the ECU 20 calculates the duty ratio DUTY by summing up Gp, Gi and Gd (DUTY=Gp+Gi+Gd), and then returns to the initial routine in FIG. 13.

Figure 15:
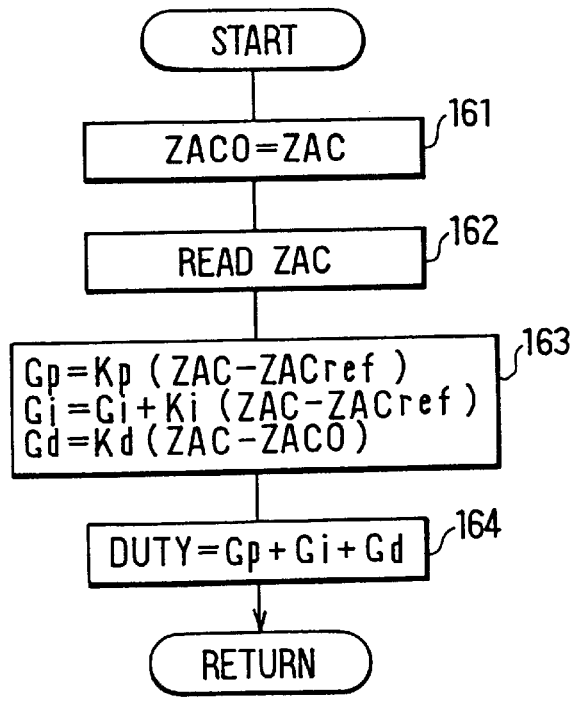
FIG. 15 is a flowchart showing a feedback control routine of the element resistance ZAC according to the first embodiment of the present invention.

The routine shown in FIG. 15 (i.e., the operation of Step 160 in FIG. 13) will now be described. The ECU 20 sets at Step 161 the element resistance ZAC of the preceding routine to the previous value "ZAC0", and reads out at subsequent Step 162 the detected element resistance ZAC (i.e., the detected value in FIG. 12). In Step 163, moreover, the ECU 20 calculates the proportional term Gp, the integration term Gi and the differentiation term Gd according to the following formulas:

$$Gp = Kp \cdot (ZAC - ZACref);$$
$$Gi = Gi + Ki \cdot (ZAC - ZACref);$$
and
$$Gd = Kd \cdot (ZAC - ZAC0).$$

In Step 164, the ECU 20 calculates the duty ratio DUTY by summing up the proportional term Gp, the integration term Gi and the differentiation term Gd (DUTY=Gp+Gi+Gd), and then returns to the initial routine in FIG. 13.

Figure 19:
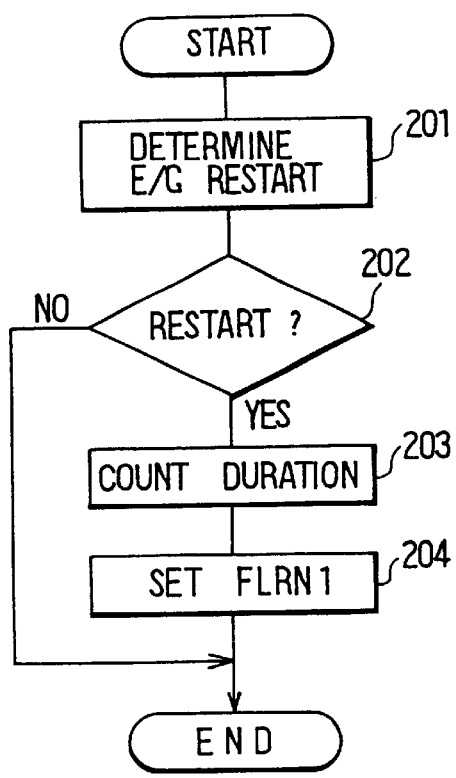
FIG. 19 is a flowchart showing a first learning routine according to the first embodiment of the present invention.
Figure 20:
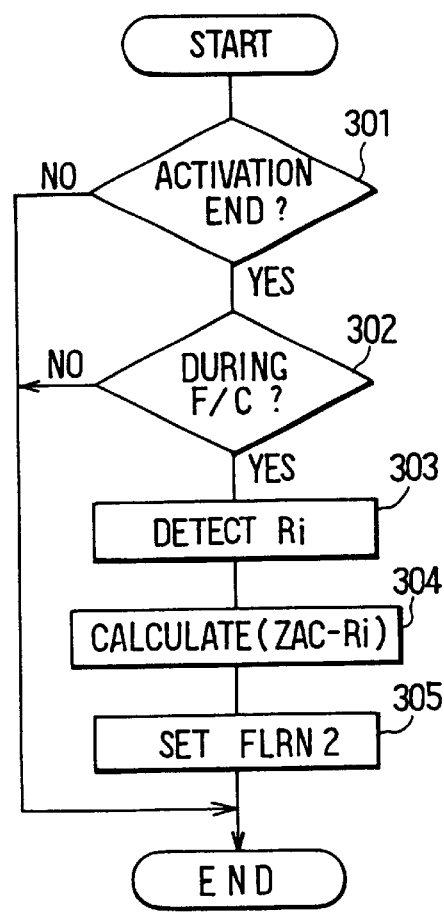
FIG. 20 is a flowchart showing a second learning routine according to the first embodiment of the present invention.
Figure 21:
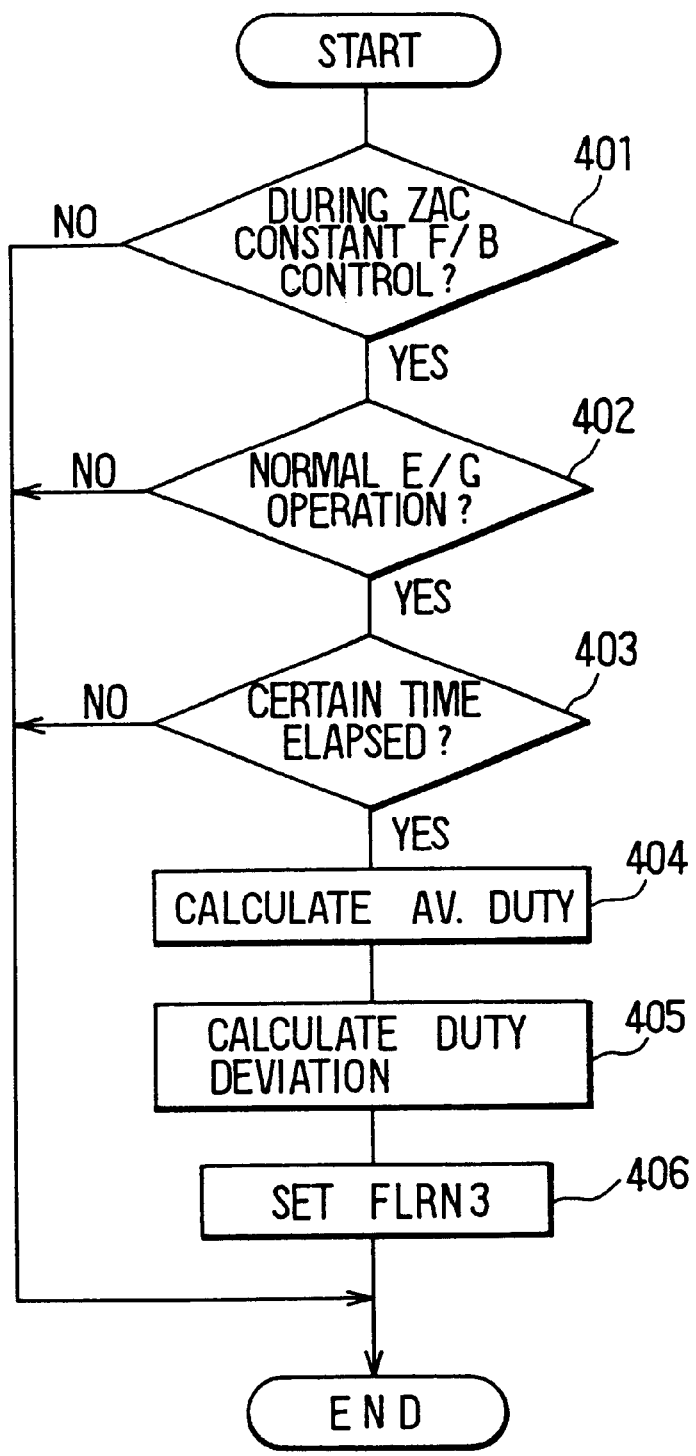
FIG. 21 is a flowchart showing a third learning routine according to the first embodiment of the present invention.

The routines for calculating the first to third learning values FLRN1 to FLRN3 will now be described with reference to the flowcharts shown in FIGS. 19 to 21. Here: FIG. 19 shows a first learning routine for calculating the first learning value FLRN1; FIG. 20 shows a second learning routine for calculating the second learning value FLRN2; and FIG. 21 shows a third learning routine for calculating the third learning value FLRN3. These individual routines are executed for a time period of 128 ms, for example, by the ECU 20. Here, the updatings of the learning values in FIGS. 19 to 21 may be executed once after the IG ON, for example. When the learning is completed, therefore, a flag indicating it is set so that the same operation may not be executed later.

First of all, the routine in FIG. 19 will be described. The ECU 20 determines at first Step 201 a restart of the engine 10. This restart determination is based on the following various conditions that:

the engine water temperature is not higher than a predetermined level (e.g., 35° C.);

the intake temperature is not higher than a predetermined level (e.g., 20° C.);

the element resistance is not lower than a predetermined level (e.g., 3 KΩ); and the heater resistance is not higher than a predetermined level (e.g., 3 Ω).

It is determined that the engine is not at the restart if all the various conditions are satisfied, and it is determined that the engine is at the restart if any of the conditions is not satisfied.

When it is determined that the engine is not at the restart (that is, when it is determined YES in Step 202), the ECU 20 advances to Step 203 to count the duration for activating the A/F sensor 30. For counting this duration, a counter, which counts up when the ignition switch is turned on, is employed. For example, as shown in FIG. 23, it is determined that the sensor is activated if any one of the following cases is satisfied:

when the change in the sensor current is greater than or equal to a predetermined determination value;

when the accumulated value of the sensor current is greater than or equal to a predetermined determination value;

when the element resistance is less than or equal to a predetermined determination value (e.g., 1 KΩ);

when the heater resistance is greater than or equal to a predetermined determination value (e.g., 4 Ω);

when the element temperature is greater than or equal to a predetermined determination value (e.g., 600° C.); and when the heater temperature is greater than or equal to a predetermined determination value (e.g., 650° C.).

The duration for the sensor activation is determined by the counted value. The determination for the sensor activation used herein, does not necessarily have the same meaning as the activation determination (at time t13 in FIG. 9) in the heater control of FIG. 13, but may be a tentative parameter for the sensor activation determination.

Figure 22A:
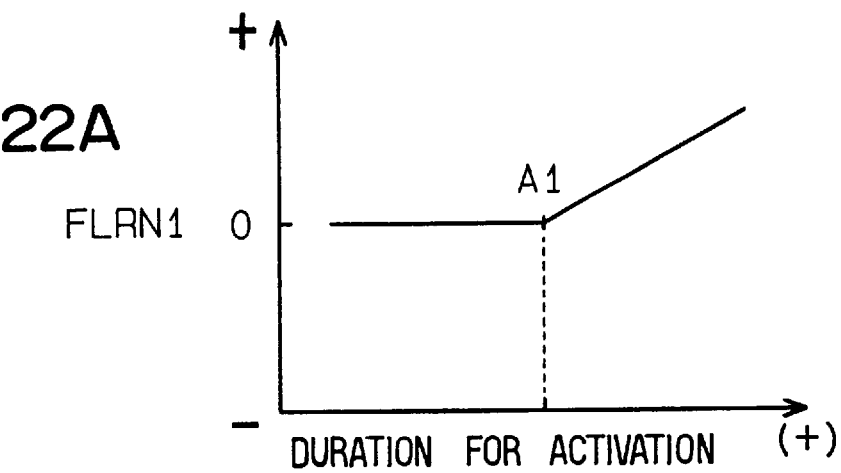
FIGS. 22A to 22C are diagrams for determining learning values FLRN1 to FLRN3 according to the first embodiment of the present invention.

After this, the ECU 20 sets, in Step 204, the first learning value FLRN1 in accordance with the duration for the sensor activation by following the relation shown in FIG. 22A, for example, and then ends this routine. The learning value FLRN1 thus set is stored (memorized) at an arbitrary time in the backup memory 20a of the ECU 20. According to FIG. 22A, the positive learning value FLRN1 is set when the duration for the activation reaches or exceeds the predetermined value A1. When the A/F sensor 30 is deteriorated, for example, the duration for the activation increases, so that the learning value FLRN1 is set at a value of "0" or greater.

The routine shown in FIG. 20 will now be described. In Step 301, the ECU 20 determines whether or not the activation of the A/F sensor 30 has been completed. In Step 302, the ECU 20 determines whether or not the fuel is being cut (F/C). If it is determined YES in both of Steps 301 and 302, the ECU 20 advances to Step 303, to detect a sensor internal resistance Ri at the timing of the F/C.

Figure 24:
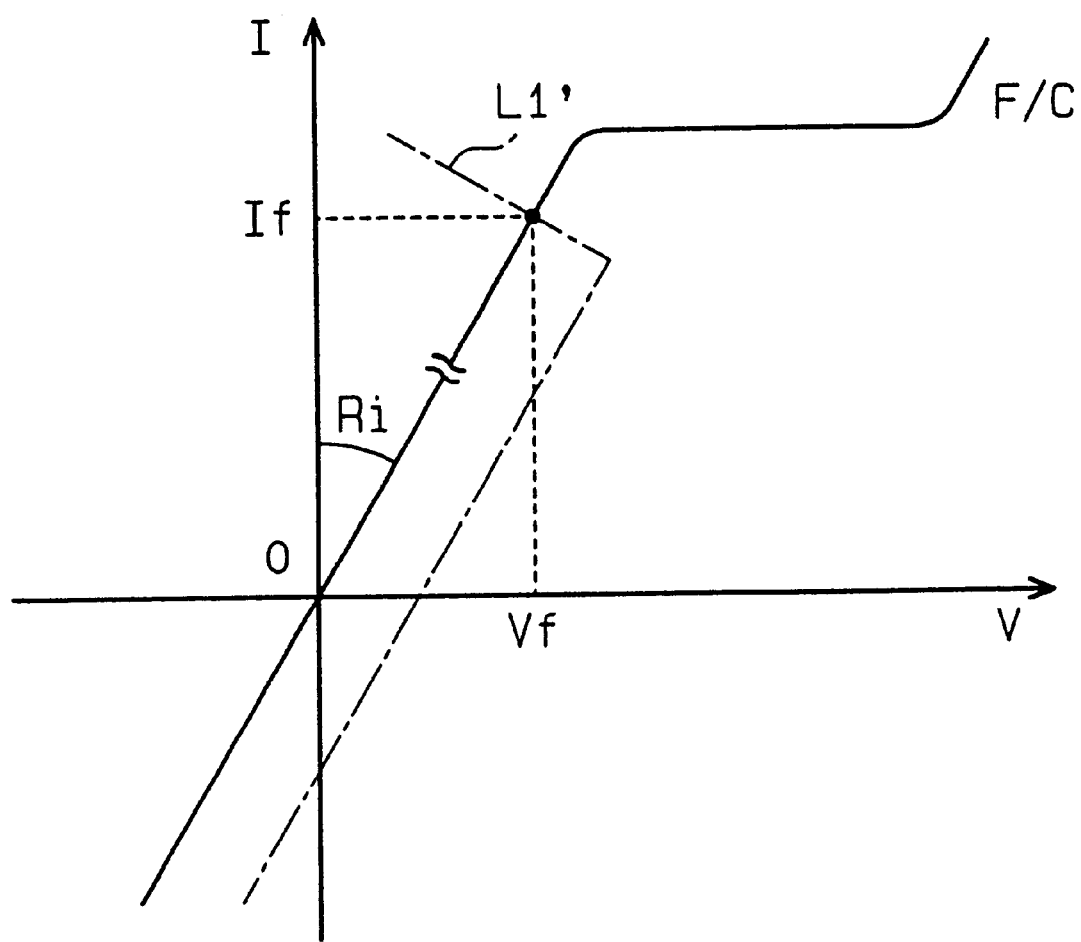
FIG. 24 is a graph illustrating a relationship between an applied voltage Vf and a sensor current If at a feedback control according to the first embodiment of the present invention.
Figure 25A:
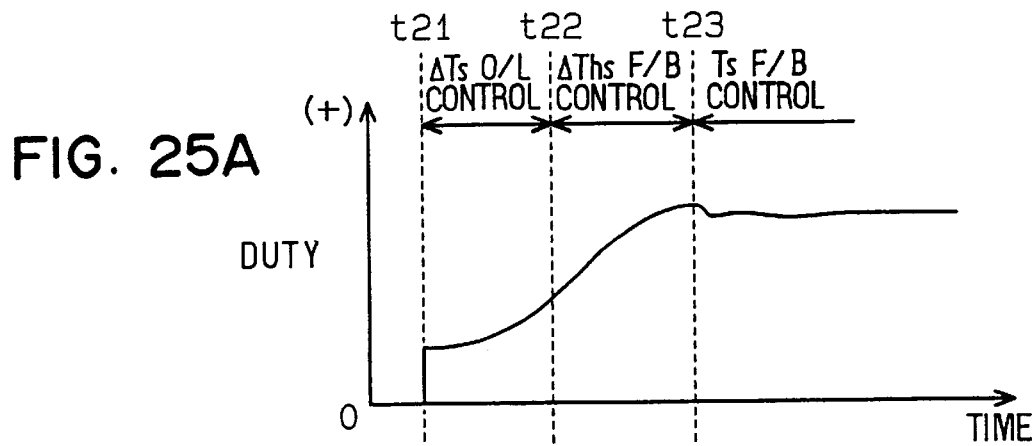
FIGS. 25A to 25D are time charts for explaining operations according to a second embodiment of the present invention.
Figure 25B:
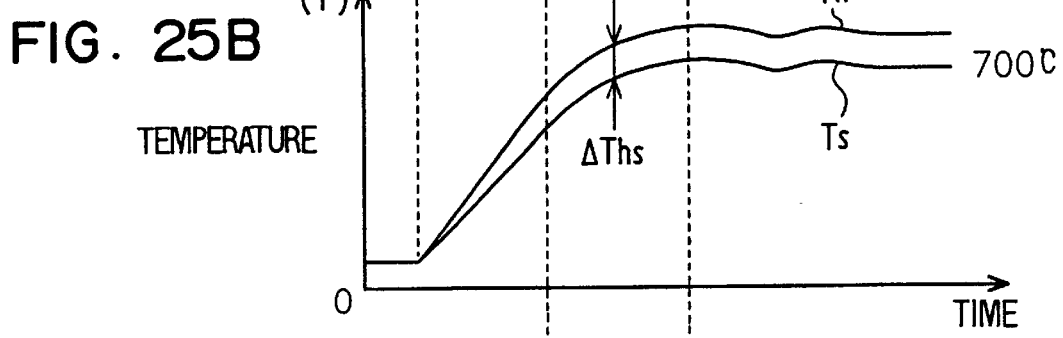
Figure 25C:
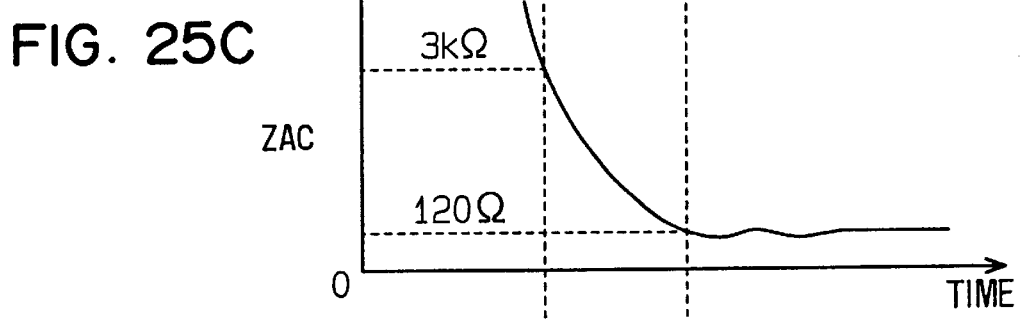
Figure 25D:
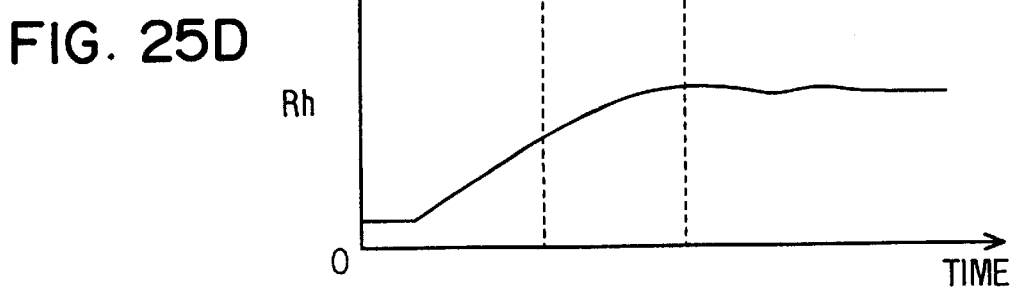

In short, during the F/C, the A/F is in an extremely lean state, and a sensor current If is detected by applying a voltage Vf in the resistance dominant region while using a chain line L1' shown in FIG. 24. Then, the sensor internal resistance Ri is detected from Ri=Vf/If.

In Step 304, the ECU 20 calculates a difference (ZAC−Ri) between the element resistance ZAC (i.e., the detected value in FIG. 12) detected by the aforementioned sweep method and the sensor internal resistance Ri detected at the F/C.

Figure 22B:
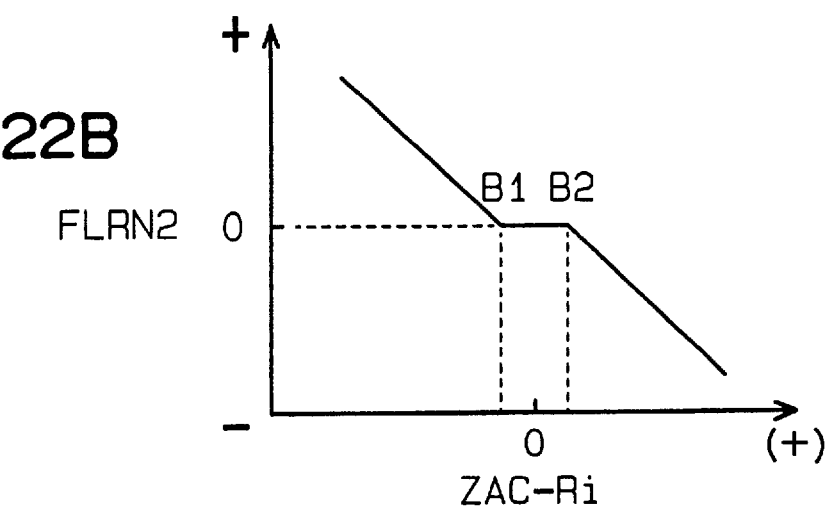

In Step 305, moreover, the ECU 20 sets the second learning value FLRN2 in accordance with the difference (ZAC−Ri) by following the relation in FIG. 22B, for example, and then ends the present routine. The set FLRN2 is stored at an arbitrary time in the backup memory 20a of the ECU 20. According to FIG. 22B, the FLRN2 is set to FLRN2=0 when the value (ZAC−Ri) is at "B1 to B2" in the vicinity of "0". A positive learning value FLRN2 is set when (ZAC−Ri)<B1, and a negative learning value FLRN2 is set when (ZAC−Ri)>B2.

The routine shown in FIG. 21 will now be described. In Step 401, the ECU 20 determines whether or not the feedback control of the constant element temperature (the constant element resistance) is being executed at present. At and after time t13 in FIGS. 9A–9C, Step 401 is affirmed. In Step 402, moreover, the ECU 20 determines whether or not the engine 10 is steadily running (that is, under normal operation) at present. Furthermore, the ECU 20 determines (at Step 403) whether or not the YES state in both Steps 401 and 402 has been continued for a predetermined time period (e.g., 5 seconds).

When it is determined YES in Step 403, the ECU 20 advances to Step 404 to calculate the average DUTY from the current supply DUTY of the heater 64 for a predetermined time period (of 5 seconds). Moreover, the ECU 20 calculates, in Step 405, DUTY deviation by subtracting the preset reference DUTY from the calculated average DUTY (DUTY deviation=average DUTY−reference DUTY). Here, the reference DUTY corresponds to a standard current supply necessary for maintaining the element temperature Ts at a predetermined level during the steady running (normal engine operation) with a constant element temperature control.

Figure 22C:
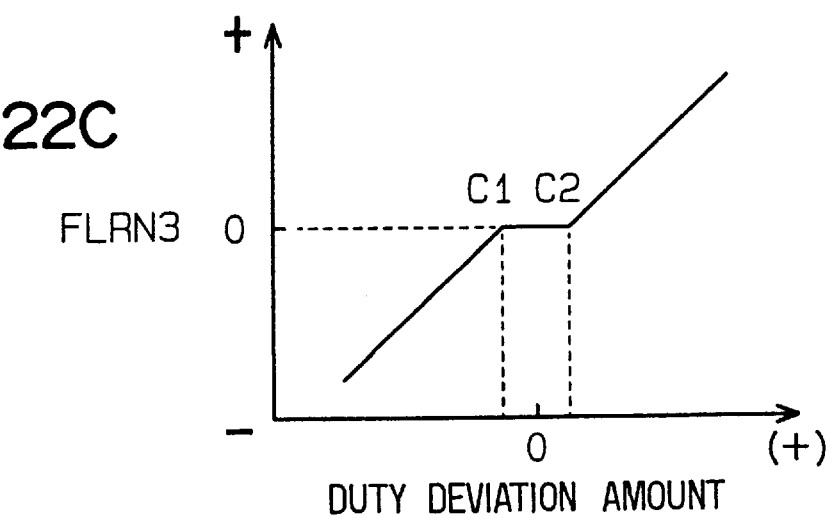
Figure 23A:
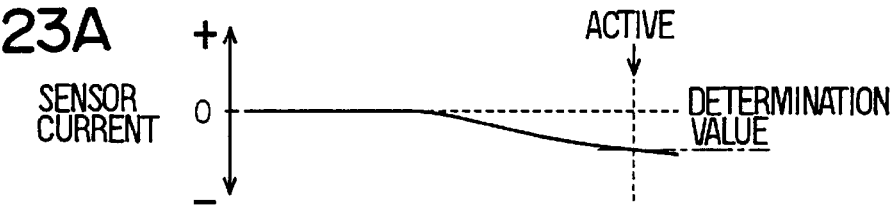
FIGS. 23A to 23F are time charts showing a behavior of an activation determination according to the first embodiment of the present invention.
Figure 23B:
Figure 23C:
Figure 23D:
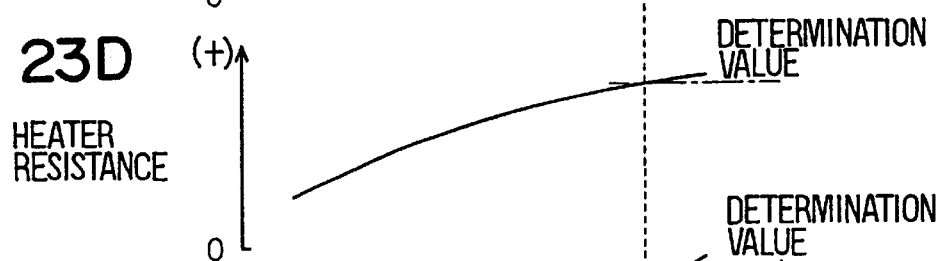
Figure 23E:
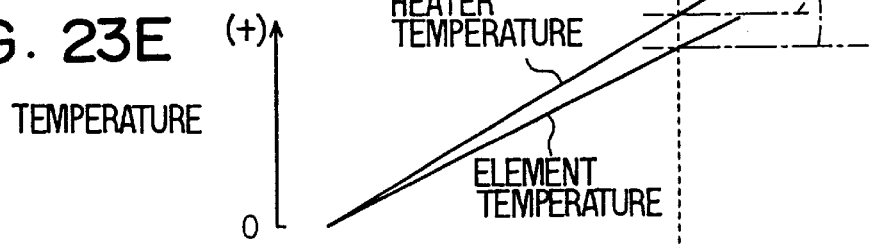
Figure 23F:
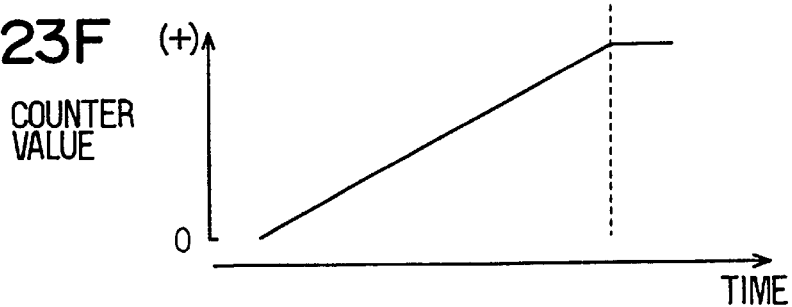

In subsequent Step 406, the ECU 20 sets the third learning value FLRN3 according to the DUTY deviation by following the relation in FIG. 22C, for example, and then ends the present routine. The set FLRN3 is stored at an arbitrary time in the backup memory 20a of the ECU 20. According to FIG. 22C, the FLRN3 is set to FLRN3=0 when the DUTY deviation is at "C1 to C2" in the vicinity of "0". Moreover, a negative learning value FLRN3 is set when the DUTY deviation<C1, and a positive learning value FLRN3 is set when the DUTY deviation >C2.

The learning values FLRN1 to FLRN3 thus calculated are suitably adopted in Steps 144 and 146 of FIG. 13 for calculating the final duty ratio Dfn (for the DUTY compensation).

According to the first embodiment of the present invention, the following effects can be achieved.

(a) The current supply to the heater is subjected to the duty control according to the element temperature changing speed ΔTs (i.e., the temperature increasing rate at the sensor element 60). Accordingly, at the temperature increasing time from the cold state of the A/F sensor 30, for example, it is possible to suppress the excessive temperature increase of the sensor element 60 and to realize a prompt activation of the sensor element 60. As a result, the temperature increasing characteristics of the A/F sensor 30 is satisfactorily maintained, and disadvantages, such as a cracking of the element or the heater and a peeling of the heater bonded surface, is prevented.

Especially, in the so-called "laminated type sensor" which is integrated by laminating the heater 64 on the solid electrolyte 61, the element cracking or heater cracking may easily be caused because these solid electrolyte 61 and heater 64 are arranged adjacent to each other. However, these problems are prevented according to the first embodiment of the present invention.

(b) The element temperature changing speed ΔTs is subjected to the open-loop control at the initial stage of the temperature rising from the cold state of the sensor. As a result, this element temperature changing rate ΔTs is properly controlled even during the time period in which ZAC can not be detected right after the engine start.

(c) It is determined whether the A/F sensor 30 is at a temperature increasing time or at a steady state after the temperature increase. If at the steady state after the temperature increase, the feedback control for the constant element temperature is executed. Once the A/F sensor 30 is activated, more specifically, the existing element temperature feedback control is executed in place of the heater control according to the element temperature changing speed ΔTs while assuming that no temperature change as abrupt as that at the temperature increasing time will occur after that activation. As a result, the proper heater control can be executed not only at the temperature increasing time but also at any other time.

(d) The element temperature Ts or its changing rate ΔTs is guarded with the predetermined maximum allowable value. As a result, the excessive heating of the sensor element 60 is prevented.

(e) On the other hand, the first to third learning values FLRN1 to FLRN3 are determined to compensate the current supply to the heater. Specifically, the current supply to the heater is compensated by:

the first learning value FLRN1 according to the duration from the cold state to the activation of the A/F sensor 30;

the second learning value FLRN2 according to the deviation (ZAC−Ri) compared between the sensor internal resistance Ri detected at the fuel cut time and the element resistance ZAC detected by the sweep method; and the third learning value FLRN3 according to the difference between the current supply DUTY at the steady running of the engine and the standard value of the preset current supply DUTY.

Accordingly, even if the A/F sensor 30 is deteriorated, disadvantage such as unexpected fluctuation of the element temperature Ts is prevented. In short, the influences upon the heater control due to the individual difference or aging of the sensor are eliminated.

(f) The learning values FLRN1 to FLRN3 described above are stored at an arbitrary time in the backup memory 20a, and are updated, if necessary. As a result, the learning values FLRN1 to FLRN3 may be calculated, only if necessary, so that the heater control is executed efficiently and properly.

(g) Moreover, the compensation values FK1 to FK4 are determined to compensate the current supply to the heater. Specifically, the current supply to the heater is compensated by:

the compensation value FK1 according to the voltage level of the battery power supply +B;

the compensation value FK2 according to the exhaust gas temperature;

the compensation value FK3 according to the initial heater resistance at the engine start; and the compensation value FK4 according to the harness resistance between the +B−the heater 64−the GND.

Accordingly, a proper heater control continues according to the engine running conditions even when the running conditions of the engine 10 sequentially change. As a result, the control accuracy of the current supply to the heater is improved.

In the first embodiment, when the current supply control of the heater (in the routine of FIG. 13), the element resistance ZAC is converted into the element temperature Ts, which is used to control the "element temperature changing speed ΔTs". However, the "element resistance changing speed" may be controlled without converting the element resistance ZAC into the element temperature Ts, instead.

(Second Embodiment)

A second embodiment of the present invention will now be described. In this and the following embodiments, the components and processes which are substantially the same to those in the first embodiment are assigned the same reference numerals.

An air/fuel ratio detecting device according to the a second embodiment will now be described with reference to FIGS. 25 to 28. This second embodiment is characterized in that the current supply control to the heater 64 is executed according to a temperature difference (a temperature difference ΔThs) between the element temperature Ts and a heater temperature Th.

First of all, the summary of the operations will be described with reference to the time charts shown in FIGS.

25A to 25D. FIGS. 25A to 25D illustrate the procedures in which the temperature of the A/F sensor 30 is increased from a cold state at a cold start of the engine 10.

When the ignition key is turned on at time t21, the open-loop control of the element temperature changing speed (rate) ΔTs using a map is started. In short, the current supply duty of the heater 64 gradually increases according to the elapsing of time, so that the element temperature Ts (the temperature of the solid electrolyte) and the heater temperature Th gradually increase accordingly.

At time t22 when the element resistance ZAC is less than a predetermined level (e.g., 3 KΩ in this embodiment) during the temperature increasing, the heater control is switched from the prevailing open-loop control of the element temperature changing rate ΔTs to the feedback control of the temperature difference (the temperature difference ΔThs) between the element temperature Ts and the heater temperature Th. At a time period from t22 to t23, more specifically, the current supply duty is determined by executing the feedback control to the target level for the difference (the temperature difference ΔThs) between the element temperature Ts and the heater temperature Th.

At later time t23 when the element resistance ZAC goes down to the determined value (e.g., 120 Ω in this embodiment) of the activation completion, the foregoing feedback control of the temperature difference ΔThs ends, and the feedback control at a constant element temperature (or at a constant element resistance) starts in place of this control. At and after time t23, more specifically, the current supply duty is determined by feedback-controlling the element temperature Ts to a predetermined target temperature (e.g., 700° C.).

Figure 26:
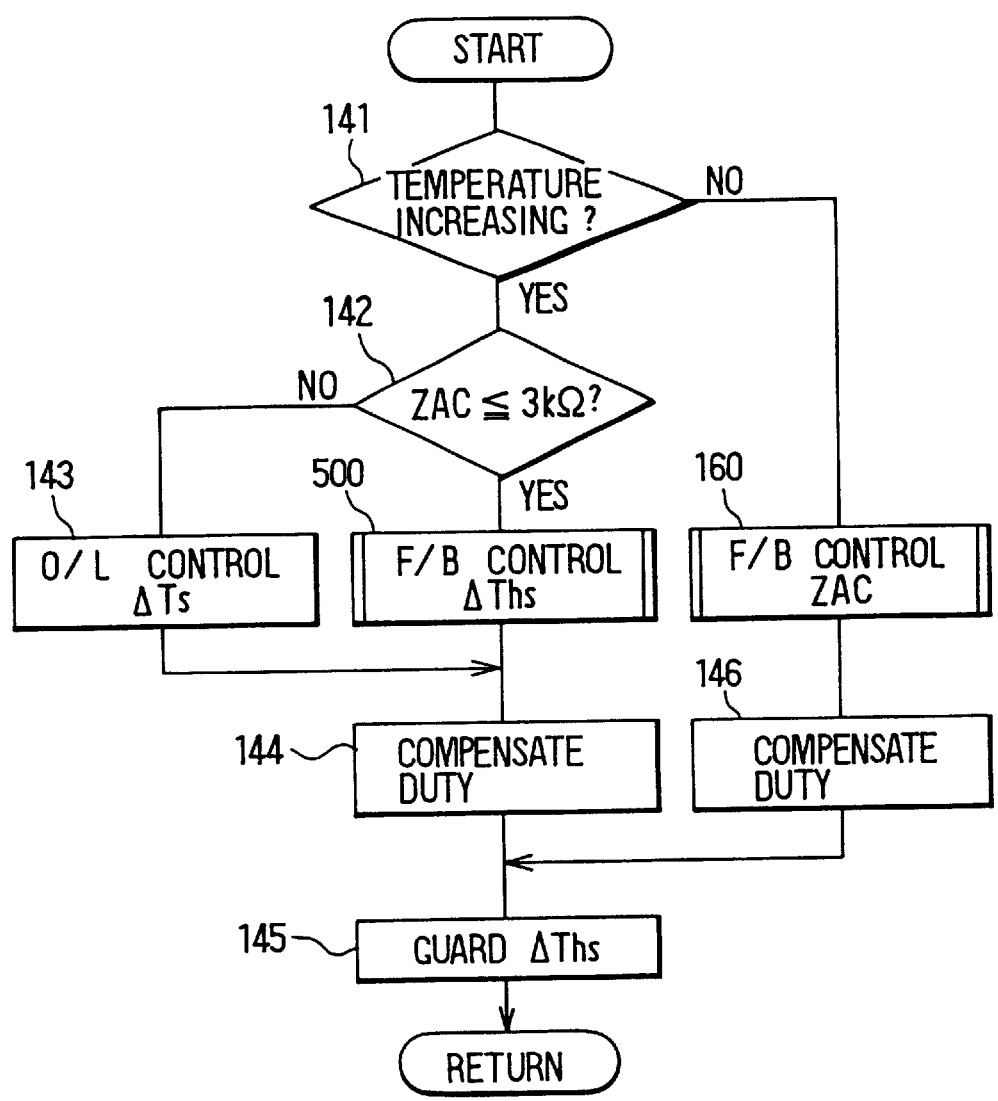
FIG. 26 is a flowchart showing a control routine for a heater current according to the second embodiment of the present invention.

FIG. 26 shows a current supply control routine for the heater according to the second embodiment of the present invention. The current supply control routine in FIG. 26 is executed by ECU 20 in place of the routine in FIG. 13. A difference between FIG. 13 and FIG. 26 is to execute Step 500 in FIG. 26 in place of Step 150 in FIG.13.

While the temperature of the sensor is increasing and when ZAC≦3 KΩ (that is, when it is determined YES in both Steps 141 and 142), the ECU 20 advances to Step 500, at which it feedback-controls the difference (the temperature difference ΔThs) between the element temperature Ts and the heater temperature Th to a predetermined value in accordance with the later-described routine shown in FIG. 27. Specifically, the duty ratio DUTY for the heater current supply is so determined by employing the PID control method that the prevailing temperature difference ΔThs and a predetermined target value ΔThsref may be equalized. For a time period of t22 to t23 in FIGS. 25A–25D, for example, the feedback control of the temperature difference ΔThs is executed in Step 500.

In this case, the temperature difference ΔThs between the element temperature Ts and the heater temperature Th is guarded with its own maximum allowable value (e.g., about 200° C.) so that the current supply DUTY may be limited to "0" or a level (e.g., about 0.1 to 1%) ensuring the drop of the element temperature, if the maximum allowable value is exceeded.

Figure 27:
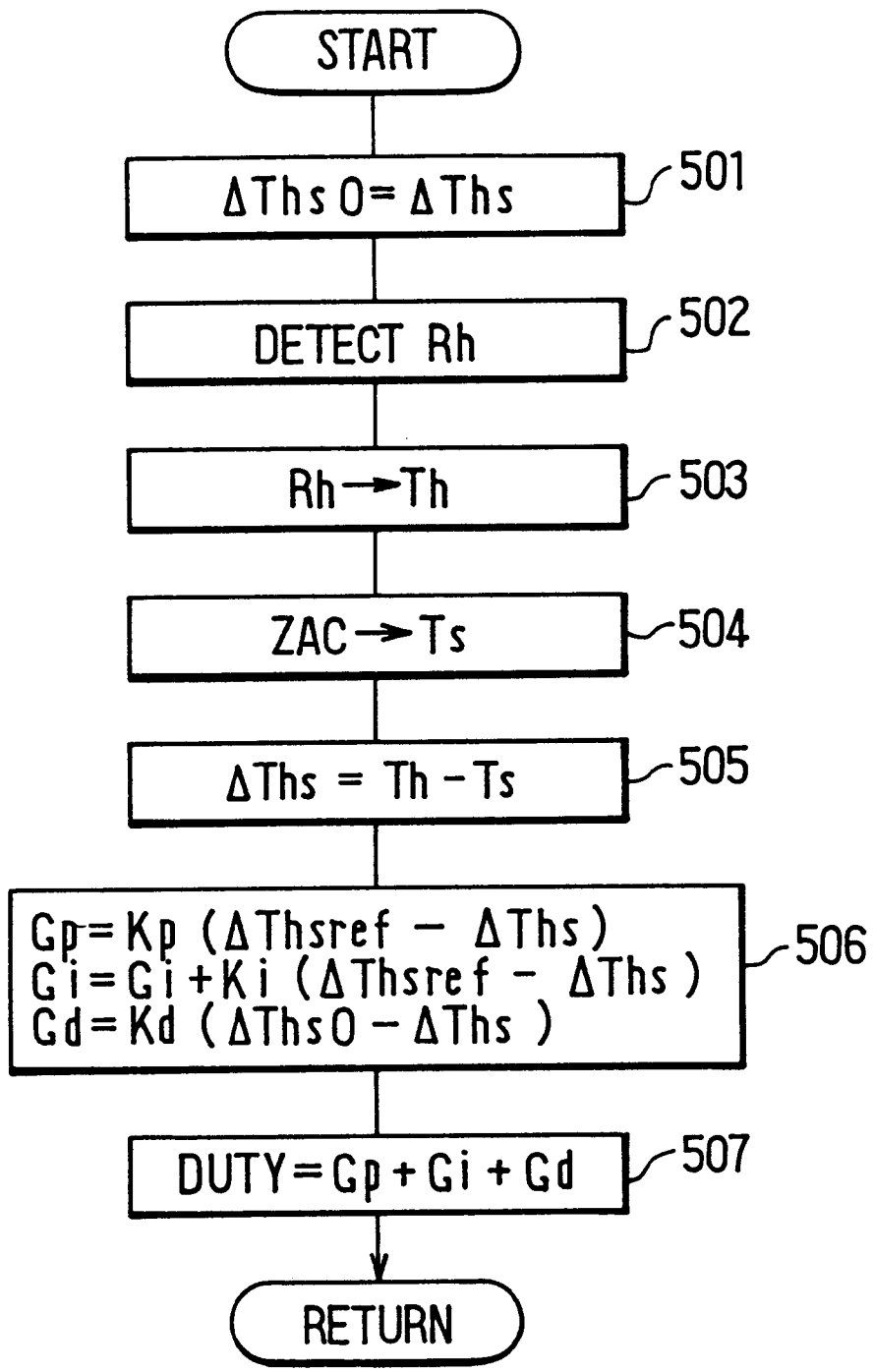
FIG. 27 is a flowchart showing a feedback control routine for a temperature difference $\Delta Ths$ according to the second embodiment of the present invention.

FIG. 27 shows a feedback control routine of the temperature difference ΔThs. In Step 501, the ECU 20 sets the preceding temperature difference ΔThs (i.e., the difference between the heater temperature Th and the element temperature Ts) to the preceding value "ΔThs0", and detects heater resistance Rh in subsequent Step 502. At this time, the voltage Vh between the two terminals of the heater 64 and the heater current Ih are fetched from the heater control circuit 25, and the heater resistance Rh is detected from the fetched values Vh and Ih (Rh=Vh/Ih).

Figure 28:
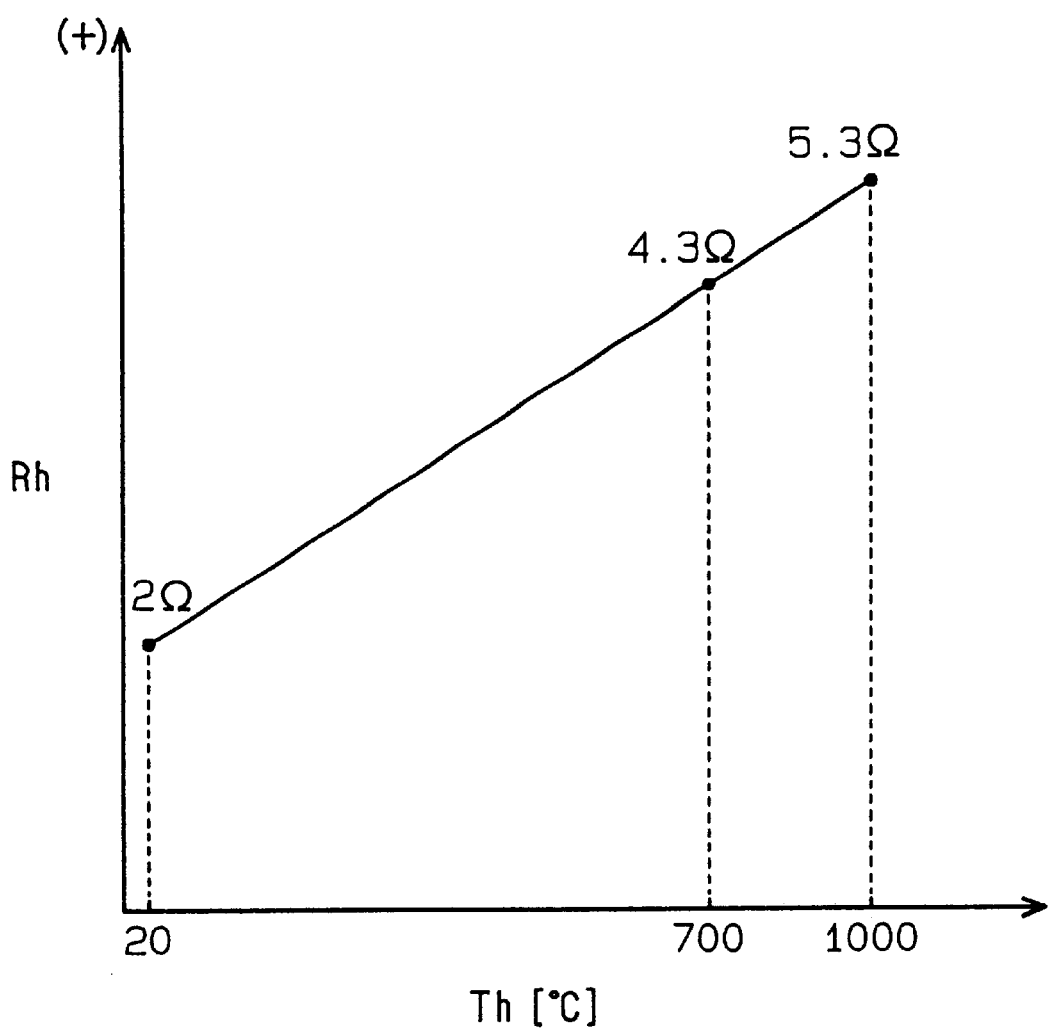
FIG. 28 is a graph illustrating a relationship between a heater resistance Rh and a heater temperature Th according to the second embodiment of the present invention.

After this, the ECU 20 converts at Step 503 the heater resistance Rh into the heater temperature Th in accordance with the relation in FIG. 28. In Step 504, the ECU 20 converts the element resistance ZAC into the element temperature Ts in accordance with the relation in FIG. 17.

Moreover, the ECU 20 determines in Step 505 the temperature difference ΔThs between the element (the solid electrolyte) and the heater (ΔThs=Th−Ts), and calculates in Step 506 the proportional term Gp, the integration term Gi and the differentiation term Gd from the following Formulas:

Gp=Kp·(ΔThsref−ΔThS);
Gi=Gi+Ki·(ΔThsref−ΔThs);
and
Gd=Kd·(ΔThs0−ΔThs).

In Step 507, the ECU 20 calculates the duty ratio DUTY by summing up the proportional term Gp, the integration term Gi and the differentiation term Gd (DUTY=Gp+Gi+ Gd), and then returns to the initial routine in FIG. 26.

According to the second embodiment of the present invention, the current supply to the heater is controlled according to the temperature difference ΔThs between the element temperature Ts and the heater temperature Th. As a result, as in the first embodiment, it is possible to keep the temperature increasing characteristics of the A/F sensor 30 and to prevent the disadvantage such as the element cracking. If the heater temperature Th becomes excessive over the element temperature Ts, more specifically, there may be caused an abrupt temperature increase of the solid electrolyte 61, which can be eliminated by that construction.

In the second embodiment, moreover, the heater resistance is converted into the heater temperature in Step 503 of FIG. 27, and the element resistance is converted into the element temperature in Step 504. After this, in Steps 505 and 506, the heater current supply control is executed based on the temperature difference between the element and the heater. Since there are constant relations between the heater resistance and the heater temperature and between the element resistance and the element temperature, however, the heater current supply control corresponding to Steps 505 and 506 may be executed directly from the heater resistance and the element resistance while omitting the resistance/ temperature conversions in Steps 503 and 504. According to this modification, also, there can be achieved the effects similar to those in the second embodiment.

(Third Embodiment)

A third embodiment of the present invention will now be described with reference to FIGS. 29 to 32. This embodiment is characterized in that the current supply control of the heater 64 is executed according to a changing speed of the heater resistance Rh (or the heater temperature Th) during the temperature increase at the A/F sensor 30.

Figure 29A:
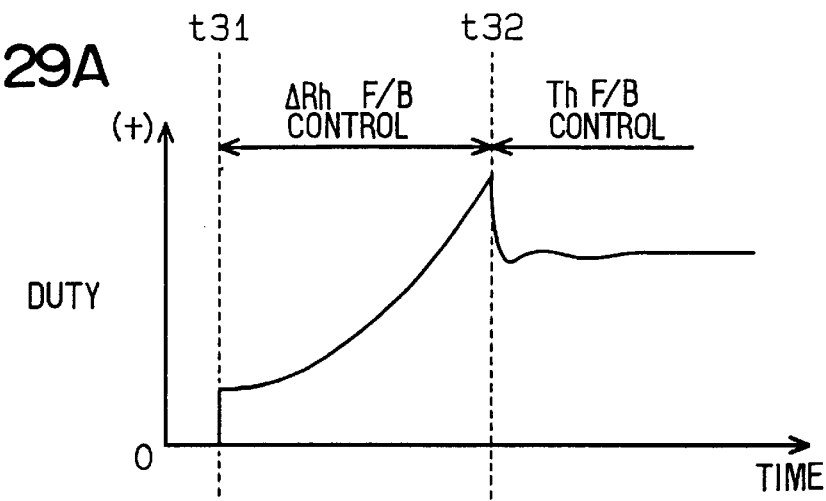
FIGS. 29A to 29C are time charts for explaining operations according to a third embodiment of the present invention.
Figure 29B:
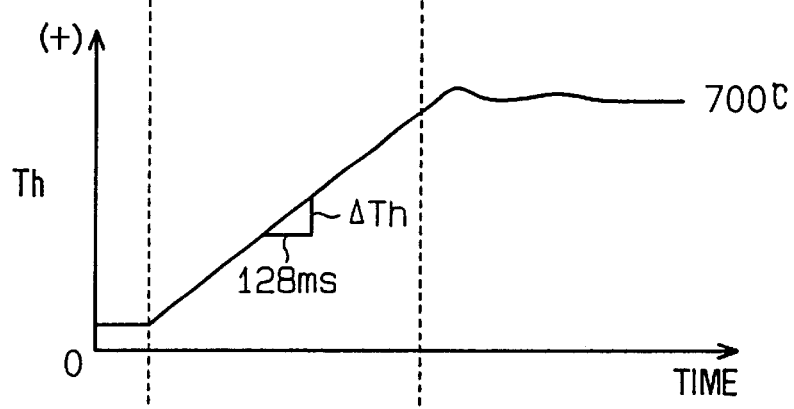
Figure 29C:
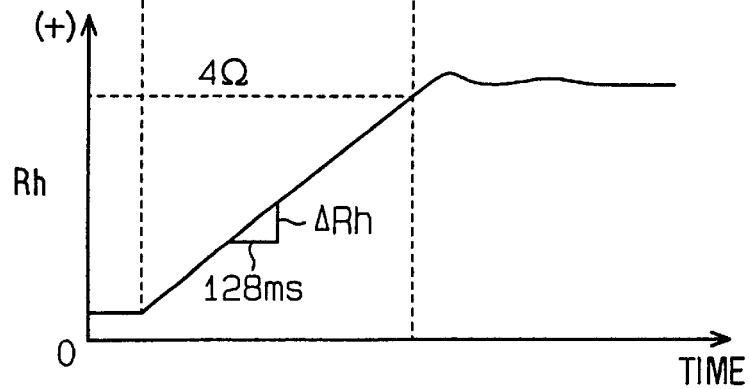

First of all, the summary of the operations in the third embodiment of the present invention will now be described with reference to the time charts of FIGS. 29A to 29C. FIGS. 29A to 29C illustrate the procedures in which the temperature of the A/F sensor 30 is increased from a cold state at a cold starting time of the engine 10.

When the ignition key is turned on at time t31, the heater resistance Rh (or the heater temperature Th) is detected from the beginning. Then, the feedback control is executed to determine the current supply duty so that the changing speed (rate) ΔRh of the heater resistance Rh (or the changing speed ΔTh of the heater temperature Th) may conform with a predetermined target value. The feedback control of this heater resistance changing rate ΔRh is continued until the completion of the activation, that is, the heater resistance Rh becomes 4 Ω.

At time t32 of Rh=4 Ω, the feedback control of the heater resistance changing rate ΔRh is ended and replaced by the feedback control at a constant heater temperature (or at a constant heater resistance). At and after time t32, more specifically, the current supply duty is determined by feedback-controlling the heater temperature Th to a predetermined target value (e.g., 700° C.). Since the feedback control at the "constant heater temperature" and the feedback control at the "constant heater resistance" are substantially identical, however, the feedback control at the constant heater resistance is executed (that is, the heater resistance Rh is fed back to the target value) in this embodiment.

Figure 30:
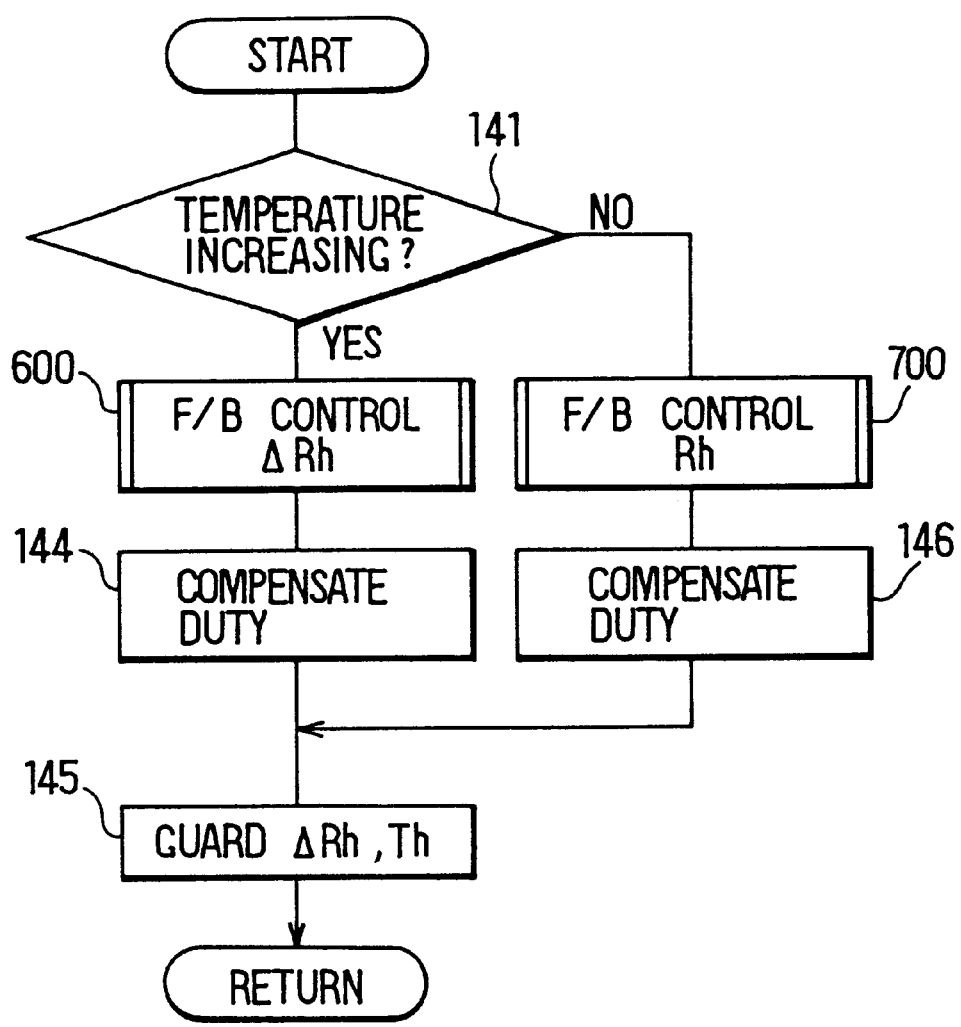
FIG. 30 is a flowchart showing a control routine for a heater current according to the third embodiment of the present invention.

FIG. 30 shows a heater current supply control routine in the third embodiment of the present invention, which is executed by ECU 20 in place of the routine shown in FIG. 13. Differences between FIG. 13 and FIG. 30 are to execute the operation in Step 600 in FIG. 30 in place of Steps 142, 143 and 150 in FIG. 13, and to execute the operation in Step 700 in place of the Step 160 in FIG. 13.

While the sensor temperature is increasing (that is, when it is determined YES in Step 141), the ECU 20 advances to Step 600 to feed back the heater resistance changing rate ΔRh to a predetermined value in accordance with the later-described routine shown in FIG. 31. Specifically, the duty ratio DUTY for the current supply is so determined by employing the PID control method that the prevailing heater resistance changing rate ΔRh and the predetermined target level ΔRhref may be conformed. For a time period from t31 to t32 in FIGS. 29A to 29C, for example, the feedback control of ΔRh in Step 600 is executed.

While the sensor temperature is not increasing (that is, when it is determined NO in Step 141), the ECU 20 advances to Step 700, at which the heater resistance Rh is feedback-controlled to a predetermined value in accordance with the later-described routine in FIG. 32. Specifically, the duty ratio DUTY for the heater current supply is so determined by employing the PID control method that the prevailing heater resistance Rh and the predetermined target value Rhref may be conformed. At and after time t32 in FIGS. 29A to 29C, for example, the feedback control with a constant heater resistance (with a constant heater temperature) in Step 700.

Here in the routine shown in FIG. 30, the heater resistance changing rate ΔRh may be guarded by its maximum allowable value (approximately 200° C./s), and the heater temperature Th may be guarded with its maximum allowable value (approximately 1,000 to 1,100° C.). If these maximum allowable values are exceeded, the DUTY may be limited to "0" or a value (approximately 0.1 to 1%) for ensuring the reliable drop of the heater temperature.

Figure 31:
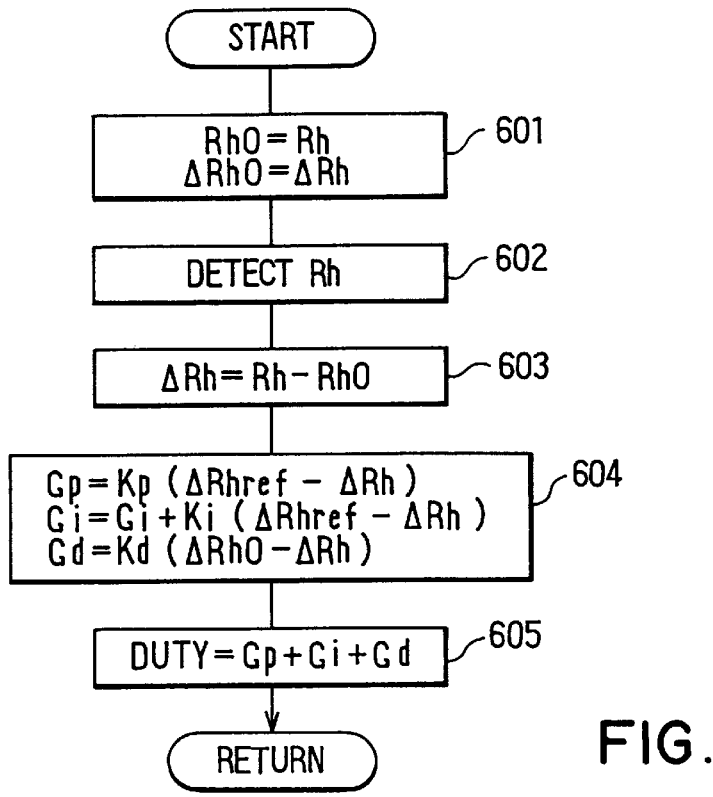
FIG. 31 is a flowchart showing a feedback control routine for a heater resistance changing rate $\Delta Rh$ according to the third embodiment of the present invention.

FIG. 31 shows a feedback control routine for the heater resistance changing rate according to the third embodiment of the present invention. The ECU 20 sets, in Step 601, the preceding heater resistance Rh to the preceding level "Rh0" and the preceding heater resistance changing rate ΔRh to the preceding level "ΔRh0", and detects in Step 602 the present value of the heater resistance Rh (Rh=Vh/Ih).

After this, the ECU 20 determines in Step 603 the heater resistance changing rate ΔRh (ΔRh=Rh−Rh0) and calculates in subsequent Step 604 the proportional term Gp, the integration term Gi and the differentiation term Gd from the following equations:

$Gp = Kp \cdot (\Delta Rhref - \Delta Rh);$ $Gi = Gi + Ki \cdot (\Delta Rhref - \Delta Rh);$ and $Gd = Kd \cdot (\Delta Rh0 - \Delta Rh).$ In Step 605, moreover, the ECU 20 calculates the duty ratio DUTY by summing up the proportional term Gp, the integration term Gi and the differentiation term Gd (DUTY=Gp+Gi+Gd), and then returns to the initial routine in FIG. 30.

Figure 32:
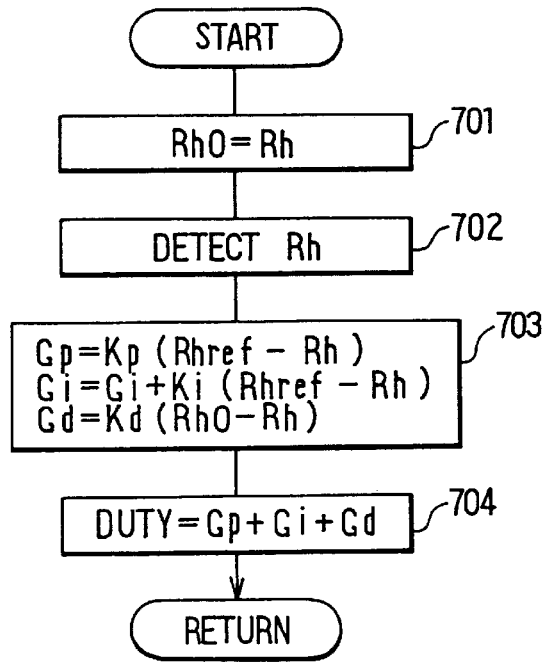
FIG. 32 is a flowchart showing a feedback control routine for a heater resistance Rh according to the third embodiment of the present invention.

FIG. 32 shows a feedback control routine for the heater resistance. The ECU 20 sets in Step 701 the preceding heater resistance Rh to the preceding value "Rh0" and detects in Step 702 the present value of the heater resistance Rh (Rh=Vh/Ih). After this, the ECU 20 calculates at Step 703 the proportional term Gp, the integration term Gi and the differentiation term Gd from the following equations:

$Gp = Kp \cdot (Rhref - Rh);$ $Gi = Gi + Ki \cdot (Rhref - Rh);$ and $Gd = Kd \cdot (Rh0 - Rh).$ In Step 704, moreover, the ECU 20 calculates the duty ratio DUTY by summing up the proportional term Gp, the integration term Gi and the differentiation term Gd (DUTY=Gp+Gi+Gd), and then returns to the initial routine in FIG. 30.

According to the third embodiment of the present invention, the current supply to the heater is controlled according to the heater resistance changing rate ΔRh. As a result, as in the first and second embodiments, it is possible to keep the temperature increasing characteristics of the A/F sensor 30 and to suppress the disadvantage such as the element cracking.

(Fourth Embodiment)

Figure 14:
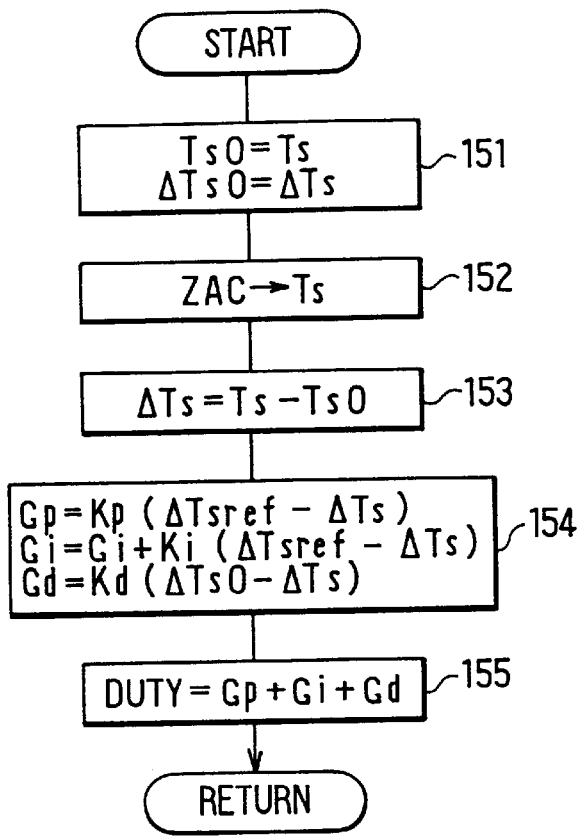
FIG. 14 is a flowchart showing a feedback control routine of an element temperature changing rate $\Delta Ts$ according to the first embodiment of the present invention.
Figure 33A:
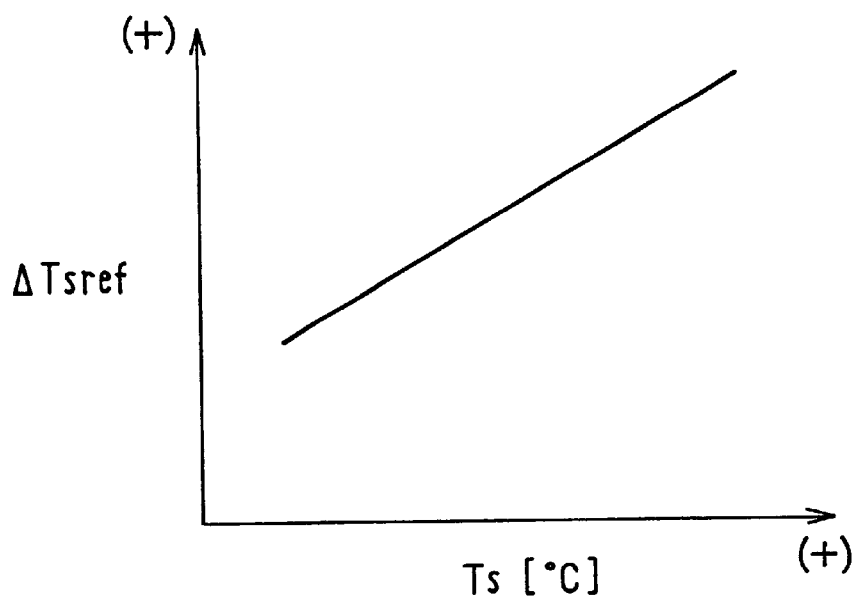
FIGS. 33A and 33B are diagrams for setting a target value $\Delta Tsref$ of an element temperature changing rate according to an element temperature Ts in a fourth embodiment of the present invention.
Figure 33B:
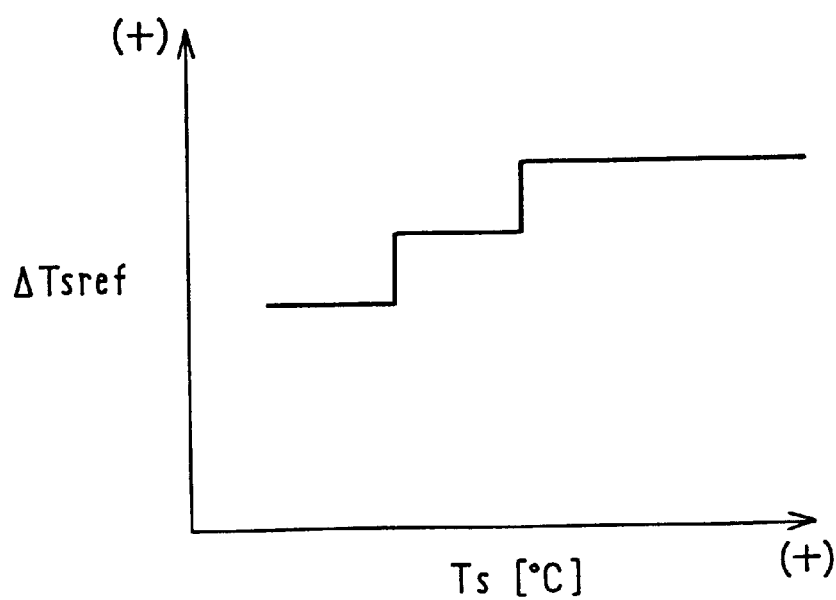

In the fourth embodiment of the present invention, the target value ΔTsref of the element temperature changing rate ΔTs is set variable in the routine (i.e., the feedback control routine of ΔTs) shown in FIG. 14 of the first embodiment. As shown in FIGS. 33A and 33B, for example, the value ΔTsref is set according to the element temperature Ts. In this case, in a high temperature range of the element temperature Ts allowing a relatively high temperature increasing rate, the value ΔTsref increases so that a relatively high current supply DUTY is set. As a result, it is possible to realize an early activation of the A/F sensor 30. Moreover, the target value may be increased gradually according to the elapsed time from the turning on of the ignition key.

As in the second and third embodiments, moreover, the target values (e.g., ΔThsref in FIG. 27 and ΔRhref of FIG. 31) during the feedback control may be set variable according to, for example, the element temperature Ts or the elapsed time.

(Fifth Embodiment)

In the first embodiment of the present invention, at the sensor temperature increasing time accompanying the cold start of the engine 10, the open-loop control and the feedback control of the element temperature changing rate ΔTs are executed (see the time periods from t11 to t12 and from t12 to t13 in FIG. 9, and FIG. 13). These controls are modified in the fifth embodiment in the following manner.

During the time period between t11 and t12 in FIG. 9, the open-loop control of the element resistance ZAC (or the element temperature Ts) is executed by using a predetermined map. During the time period between t12 and t13 in FIG. 9, moreover, the feedback control is executed to set the element resistance ZAC (or the element temperature Ts) to the target value ZACref. The feedback routine of the element resistance ZAC conforms to that of FIG. 15. At this time, the element resistance ZAC changing rate (corresponding to the temperature increasing rate of the sensor element 60) may be guarded not to exceed the predetermined maximum value. Accordingly, it is possible to keep the temperature increasing characteristics of the sensor and to suppress the disadvantage such as the element cracking.

(Sixth Embodiment)

In the third embodiment of the present invention, at the sensor temperature increasing time accompanying the cold start of the engine 10, the feedback control of the heater resistance changing rate ΔTs is executed (see t31 to t32 in FIGS. 29A to 29C, and FIG. 30). In the sixth embodiment, the feedback control is modified in the following manner.

During the time period between t31 and t32 in FIGS. 29A to 29C, the heater resistance Rh (or the heater temperature Th) is feedback-controlled to the target value Rhref. The feedback control routine of the heater resistance Rh conforms to that of FIG. 32. Here, the changing rate of the heater resistance Rh (i.e., the temperature increasing rate of the sensor element 60) may be guarded not to exceed a predetermined maximum value.

Figure 34:
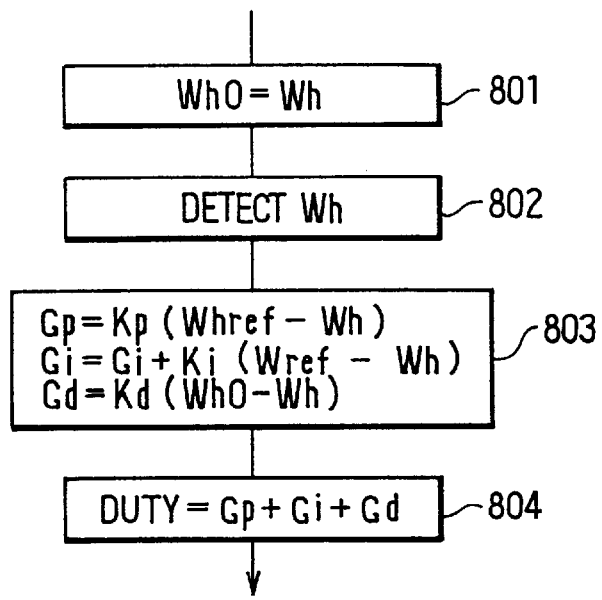
FIG. 34 is a flowchart showing a feedback control routine for a heater power Wh according to a sixth embodiment of the present invention.

Alternatively, during the time period between t31 and t32 in FIGS. 29A to 29C, a heater power Wh may be feedback-controlled to a target value Whref. This feedback routine of the heater power Wh will now be described with reference to FIG. 34.

First of all, the heater power Wh is set to the preceding value "Wh0" in Step 801;

the present value of the heater power Wh is detected in Step 802;

the proportional term Gp, the integration term Gi and the differentiation term Gd are determined from the following equations in Step 803:

Gp=Kp·(Whref−Wh)

Gi=Gi+Ki·(Whref−Wh);

and

Gd=Kd·(Wh0−Wh).

The duty ratio DUTY is calculated in Step 804 by summing up the proportional term Gp, the integration term Gi and the differentiation term Gd. At this time, the changing rate of the heater power Wh (corresponding to the temperature increasing rate of the sensor element 60) may be guarded not to exceed a predetermined maximum value.

In this case, however, the heater power Wh is determined by multiplying the heater voltage Vh by the heater current Ih. The heater power Wh may be replaced by the accumulated heater power from the turning on of the ignition key. Accordingly, it is possible to keep the temperature increasing characteristics of the sensor and to suppress the disadvantage such as the element cracking.

(Seventh Embodiment)

In the first to third embodiments of the present invention, the feedback control at the constant element temperature (or at the constant element resistance) is performed in place of the existing heater control according to the temperature increasing rate (the temperature increasing speed) of the sensor element after the sensor activation. This feature is changed in a seventh embodiment of the present invention. Even after the sensor activation, for example, the heater control according to the temperature increasing rate of the sensor element may be continuously executed instead.

(Eighth Embodiment)

Figure 35:
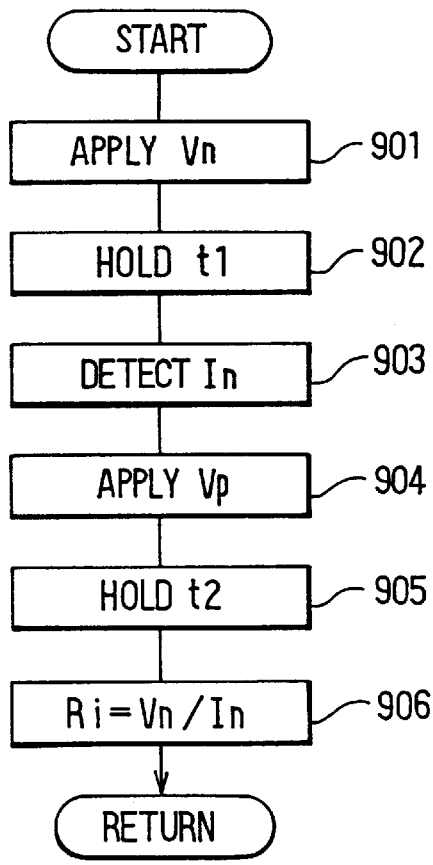
FIG. 35 is a flowchart showing a detection routine of an element resistance Ri according to an eighth embodiment of the present invention.

The "AC element resistance ZAC" is detected in the above embodiments of the present invention to detect the element resistance of the A/F sensor 30. However, the "DC element resistance Ri" is detected in an eighth embodiment instead of detecting "AC element resistance ZAC". Specifically, the Ri detecting routine, as shown in FIG. 35, is executed in place of the routine (Step 130 in FIG. 10) of FIG. 12. In FIG. 35, more specifically, the ECU 20 applies in Step 901 a negative voltage Vn to the sensor element 60. This voltage Vn has a value in a resistance dominant range which is outside the limiting current generating region, such as Vn =about −0.3 to −1 [V]. Moreover, the ECU 20 awaits in Step 902 a time period t1 (for example, several tens to several hundreds ms) for which the peak current just after the voltage change is completely converged, and detects the current value In in Step 903.

After this, the ECU 20 returns the applied voltage from the negative voltage Vn to the initial positive voltage Vp in Step 904. Moreover, the ECU 20 awaits (at Step 905) a time period t2 (e.g., several tens to several hundreds ms) for which the peak current just after the voltage change is completely converged, and then calculates at Step 906 the DC element resistance Ri from the negative voltage Vn and the current value In (or a negative current value) (Ri=Vn/In).

When the DC element resistance is detected as described above, the construction, in which a single AC voltage in a predetermined frequency region is applied to the sensor element 60, is obviated to omit the LPF 22 in FIG. 1.

In the foregoing individual embodiments, the gas diffusion resistive layer 62 includes the gas permeable layer 62a and the gas shielding layer 62b, as described with reference to FIG. 3. However, the gas shielding layer 62b may be omitted. In the embodiments, moreover, the invention is embodied in the laminated type A/F sensor. However, it may be embodied in a cup type A/F sensor instead.

In the foregoing individual embodiments, the invention is embodied in the A/F sensor for outputting a linear limiting current according to the oxygen concentration (the air/fuel ratio). However, it may be embodied in an $O_2$ sensor for outputting different voltage signals according to whether the air/fuel ratio is rich or lean. The invention may also be embodied into either a NOx sensor for detecting the NOx concentration in the exhaust gases or the so-called "complex sensor" for detecting the various components such as NOx, HC and $O_2$. The invention can also be applied to a system for metering the concentration of gas components other than the exhaust gases.

In the foregoing individual embodiments, moreover, the duty ratio DUTY is compensated with the compensation value FK or the learning value FLRN (Steps 144 and 146 in FIG. 13). However, this compensation may be omitted.

In the foregoing individual embodiments, the PID control is executed for the various feedback controls. However, the PID control may be replaced by another control such as the PI control or the P control.

Although the present invention has been described in connection with the preferred embodiments thereof with reference to the accompanying drawings, it is to be noted that various changes and modifications will be apparent to those skilled in the art. Such changes and modifications are to be understood as being included within the scope of the present invention as defined in the appended claims.

What is claimed is:

1. A gas component concentration measuring apparatus comprising:

a sensor, including a sensor element made of a solid electrolyte, for measuring a concentration of a specific gas component to be measured;

a heater for heating said sensor element according to a current supply;

heater control means for controlling said current supply to said heater during a heating of said sensor element from a cold, inactive state to a hot, activated state, in accordance with a temperature increasing rate of said sensor element, thereby to control the temperature increasing rate of the sensor element to not exceed a predetermined temperature increasing rate; and sensor changing rate determining means for detecting one of temperature and resistance of said sensor element, and for determining a changing rate of said detected one of temperature and resistance, wherein:

said heater control means controls said current supply to said heater in accordance with said changing rate determined by said sensor changing rate determining means.

2. A gas component concentration measuring apparatus according to claim 1, further comprising:

temperature increase determining means for determining whether said sensor is under a temperature increase or under a steady condition after said temperature increase, wherein;

said heater control means controls said current supply to said heater to execute a feedback control which conforms a temperature of said sensor element to a target temperature under said steady condition after said temperature increase.

3. A gas component concentration measuring apparatus according to claim 1, wherein said current supply to said heater is limited when said temperature increasing rate of said sensor element exceeds a predetermined value.

4. A gas component concentration measuring apparatus according to claim 1, wherein said current supply to said heater is compensated according to necessary time period to activate said sensor from a cold state of said sensor.

5. A gas component concentration measuring apparatus for an air/fuel ratio control system of an engine, according to claim 1, wherein;

said apparatus applies voltage to a resistance dominant region of said sensor at a fuel cut of said engine for determining an internal resistance of said sensor from a sensor current obtained by said voltage apply, and said current supply to said heater is compensated based on said determined internal resistance of said sensor.

6. A gas component concentration measuring apparatus according to claim 5, wherein;

a learning value corresponding to said compensation is stored in a backup memory, and said heater control means reads out said learning value from said backup memory to control said current supply.

7. A gas component concentration measuring apparatus according to claim 5, wherein said current supply to said heater is further compensated according to a power supply voltage.

8. A gas component concentration measuring apparatus according to claim 5, wherein said current supply to said heater is further compensated according to a temperature of said specific gas component to be measured.

9. A gas component concentration measuring apparatus according to claim 5, wherein said current supply to said heater is further compensated according to an activation state of said sensor during a temperature increase of said sensor element from a cold state of said sensor.

10. A gas component concentration measuring apparatus for an air/fuel ratio control system of an engine, according to claim 1, wherein said current supply to said heater is compensated according to a difference between a current supply amount to said heater at a steady condition of said engine and a predetermined standard value of said current supply amount to said heater.

11. A gas component concentration measuring apparatus according to claim 1, wherein said sensor is constructed by laminating said heater on said sensor element to integrate said solid electrolyte with said heater.

12. A gas component concentration measuring apparatus according to claim 1, wherein said heater control means executes an open-loop control of the increasing rate of a sensor element temperature when the heater control means determines that the temperature of the sensor element is increasing and the heater control means determines that the sensor element resistance is greater than a predetermined value.

13. A gas component concentration measuring apparatus according to claim 1, wherein said heater control means executes a feedback control for the increasing rate of a sensor element temperature when the heater control means determines that the temperature of the sensor element is increasing and the heater control means determines that the sensor element resistance is less than a predetermined value.

14. A gas component concentration measuring apparatus according to claim 1, wherein said heater control means executes feedback control of sensor element resistance when said heater control means determines that the temperature of the sensor element is not increasing.

15. A gas component concentration measuring apparatus comprising:

a sensor, including a sensor element made of a solid electrolyte, for measuring a concentration of a specific gas component to be measured;

a heater for heating said sensor element according to a current supply;

heater control means for controlling said current supply to said heater during a heating of said sensor element from a cold, inactive state to a hot, activated state, in accordance with a temperature increasing rate of said sensor element, thereby to control the temperature increasing rate of the sensor element to not exceed a predetermined temperature increasing rate; and temperature difference determining means for detecting a temperature of said sensor element and a temperature of said heater, and for determining a temperature difference between said sensor element temperature and said heater temperature, wherein:

said heater control means controls said current supply to said heater in accordance with said temperature difference determined by said temperature difference determining means.

16. A gas component concentration measuring apparatus comprising:

a sensor, including a sensor element made of a solid electrolyte, for measuring a concentration of a specific gas component to be measured;

a heater for heating said sensor element according to a current supply;

heater control means for controlling said current supply to said heater during a heating of said sensor element from a cold, inactive state to a hot, activated state, in accordance with a temperature increasing rate of said sensor element, thereby to control the temperature increasing rate of the sensor element to not exceed a predetermined temperature increasing rate; and resistance difference determining means for detecting a resistance of said sensor element and a resistance of said heater, and for determining a resistance difference between said sensor element resistance and said heater resistance, wherein:
said heater control means controls said current supply to said heater in accordance with said resistance difference determined by said resistance difference determining means.

17. A gas component concentration measuring apparatus according to claim 16, wherein said heater control means executes an open-loop control for a changing rate of one of a sensor element temperature and a sensor element resistance until said sensor element resistance is detected during a temperature increase of said sensor element from a cold state of said sensor.

18. A gas component concentration measuring apparatus for an engine, comprising:
a sensor, including a sensor element made of a solid electrolyte, for measuring a concentration of a specific gas component to be measured;
a heater for heating said sensor element to an activation temperature according to a current supply; and
heater control means for actively controlling said current supply to said heater during a heating of said sensor element from a cold, inactive state to a hot, activated state, in accordance with a temperature increasing rate of said sensor element, thereby to actively control the temperature increasing rate of the sensor element so that temperature increase rate greater than a predetermined temperature increasing rate is suppressed, wherein;
said apparatus applies voltage to a resistance dominant region of said sensor at a fuel cut of the engine for determining an internal resistance of said sensor from a sensor current obtained by said voltage application, and
said current supply to said heater is compensated based on said determined internal resistance of said sensor.

19. A gas component concentration measuring apparatus according to claim 18, wherein;
a learning value corresponding to said compensation is stored in a backup memory, and
said heater control means reads out said learning value from said backup memory to control said current supply.

20. A gas component concentration measuring apparatus according to claim 18, wherein said current supply to said heater is further compensated according to a power supply voltage.

21. A gas component concentration measuring apparatus according to claim 18, wherein said current supply to said heater is further compensated according to a temperature of said specific gas component to be measured.

22. A gas component concentration measuring apparatus according to claim 18, wherein said current supply to said heater is further compensated according to an activation state of said sensor during a temperature increase of said sensor element from a cold state of said sensor.

23. A gas component concentration measuring apparatus according to claim 18, wherein said sensor is constructed by laminating said heater on said sensor element to integrate said solid electrolyte with said heater.

24. A gas component concentration measuring apparatus for an engine, comprising:
a sensor, including a sensor element made of a solid electrolyte, for measuring a concentration of a specific gas component to be measured;
a heater for heating said sensor element to an activation temperature according to a current supply; and
heater control means for actively controlling said current supply to said heater during a heating of said sensor element from a cold, inactive state to a hot, activated state, in accordance with a temperature increasing rate of said sensor element, thereby to actively control the temperature increasing rate of the sensor element so that a rate of temperature increase rate greater than a predetermined temperature increasing rate is suppressed, wherein;
said current supply to said heater is compensated according to a difference between a current supply amount to said heater at a steady condition of the engine and a predetermined standard value of said current supply amount to said heater.

* * * * *